United States Patent
Gabbay

(10) Patent No.: US 10,431,059 B2
(45) Date of Patent: Oct. 1, 2019

(54) NAVIGATIONAL DEVICE AND METHODS

(71) Applicants: TREKACE TECHNOLOGIES LTD, Kfar Saba (IL); Isidor-Ronen Gabbay, Kfar Saba (IL)

(72) Inventor: Isidor-Ronen Gabbay, Tel Aviv (IL)

(73) Assignees: Trekace Technologies Ltd., Kfar Saba (IL); Ronen Gabbay, Kfar Saba (IL)

( * ) Notice: Subject to any disclaimer, the term of this patent is extended or adjusted under 35 U.S.C. 154(b) by 0 days.

(21) Appl. No.: 15/541,492

(22) PCT Filed: Jan. 11, 2016

(86) PCT No.: PCT/IL2016/000001
§ 371 (c)(1),
(2) Date: Jul. 5, 2017

(87) PCT Pub. No.: WO2016/113730
PCT Pub. Date: Jul. 21, 2016

(65) Prior Publication Data
US 2018/0268670 A1    Sep. 20, 2018

Related U.S. Application Data

(60) Provisional application No. 62/102,118, filed on Jan. 12, 2015.

(51) Int. Cl.
*A61F 9/08* (2006.01)
*G08B 7/06* (2006.01)
(Continued)

(52) U.S. Cl.
CPC ............ *G08B 7/066* (2013.01); *A61F 9/08* (2013.01); *G01C 21/3652* (2013.01); *G09B 21/003* (2013.01); *G09B 21/004* (2013.01)

(58) Field of Classification Search
None
See application file for complete search history.

(56) References Cited

U.S. PATENT DOCUMENTS 6,155,836 A * 12/2000 Hancock ............... G09B 19/02
                                                           2/159
2002/0111737 A1* 8/2002 Hoisko .................. G01C 21/20
                                                           701/526
(Continued)

FOREIGN PATENT DOCUMENTS

DE    102014110476 B4    10/2015
WO    2014099004A1 A1    6/2014
WO    WO-2014099004 A1 *  6/2014    ............. G01C 21/20

OTHER PUBLICATIONS

Hein et al. conTACT—A Vibrotactile Display for Computer Aided Surgery, 2007, IEEE, 0-7695-2738-8/07 (Year: 2007).*
(Continued)

*Primary Examiner* — Carlos Garcia
(74) *Attorney, Agent, or Firm* — Eva Taksel

(57) ABSTRACT

The present invention provides a wearable navigation forearm-band device for intuitive navigation of a user to his destination, the device including at least four tactile stimulus providers, each adapted to impact on different areas of a forearm of a user to provide a specific direction of movement of the user, wherein the device is adapted to receive commands from a communication apparatus to activate said vibration indicators response to a position of the user.

24 Claims, 13 Drawing Sheets

(51) Int. Cl.
　　　 G01C 21/36　　　(2006.01)
　　　 G09B 21/00　　　(2006.01)

(56) References Cited

U.S. PATENT DOCUMENTS

| | | | |
|---|---|---|---|
| 2007/0016425 | A1 | 1/2007 | Ward |
| 2008/0120029 | A1* | 5/2008 | Zelek .................... G01C 21/20 701/469 |
| 2013/0218456 | A1* | 8/2013 | Zelek ................ G01C 21/3652 701/412 |
| 2014/0184384 | A1* | 7/2014 | Zhu ...................... G09B 21/003 340/4.12 |
| 2015/0334530 | A1* | 11/2015 | Scott ..................... G06Q 50/22 455/456.1 |
| 2016/0329837 | A1* | 11/2016 | Kataoka ................ H02N 2/142 |
| 2018/0040258 | A1* | 2/2018 | Kouache ............ G01C 21/3652 |
| 2018/0106636 | A1* | 4/2018 | Hu ........................ A61H 3/061 |

OTHER PUBLICATIONS

Oliveira et al., Tactile Interface for Navigation in Underground Mines, 2014, IEEE, 978-1-4799-4261-9/14 (Year: 2014).*

Paneels et al., What's Around Me? Multi-Actuator Haptic Feedback on the Wrist, Apr. 14-18, 2013, IEEE, IEEE World Haptics Conference, 978-1-4799-0088-6/13/$31.00 © 2013 IEEE, pp. 407-412 (Year: 2013).*

Caswell et al., Design of a Forearm-Mounted Directional Skin Stretch Device, Mar. 4-7, 2012, IEEE, IEEE Haptics Symposium 2012, 978-1-4673-0809-0/12/$31.00 © 2012 IEEE, pp. 365-370 (Year: 2012).*

Weber et al., Evaluation of a Vibrotactile Feedback Device for Spatial Guidance, Jun. 21-24, 2011, IEEE, IEEE World Haptics Conference 2011, 978-1-4577-0298-3/11/$26.00 © 2011 IEEE, pp. 349-354 (Year: 2011).*

Claire Lee et al., AirTouch: Synchronizing in-air hand gesture and on-body tactile feedback to augment mobile gesture interaction, 2011, IEEE, 1550-4816/11 $26.00 © 2011 IEEE DOI 10.1109/ISWC.2011.27, pp. 3-10 (Year: 2011).*

Johnson et al., A Navigation Aid for the Blind Using Tactile-Visual Sensory Substitution, Aug. 30-Sep. 3, 2006, IEEE, Proceedings of the 28th IEEE EMBS Annual International Conference, 1-4244-0033-3/06/$20.00 ©2006 IEEE, pp. 6289-6292 (Year: 2006).*

Spelmezan et al., Tactile Motion Instructions for Physical Activities, Apr. 4-9, 2009, CHI 2009, Boston, Massachusetts, USA. Copyright 2009 ACM 978-1-60558-246-7/09/04 . . . $5.00. (Year: 2009).*

Nakamura et al., Multimodal Presentation Method fora Dance Training System, Apr. 2-7, 2005, CHI 2005, Portland, Oregon, USA. ACM 1-59593-002-7/05/0004, pp. 1685-1688 (Year: 2005).*

Piateski et al., Vibrotactile Pattern Recognition on the Arm and Torso, 2005, Proceedings of the First Joint Eurohaptics Conference and Symposium on Haptic Interfaces for Virtual Environment and Teleoperator Systems 0-7695-2310-2/05 $20.00 © 2005 IEEE (Year: 2005).*

Cholewiak et al., Vibrotactile localization on the arm: Effects of place, space, and age, Manuscript received Nov. 12, 2002; revision accepted for publication Mar. 19, 2003, Psychonomic Society, Perception & Psychophysics 2003, 65 (7), pp. 1058-1077 (Year: 2002).*

Schatzle et al., Evaluation of Vibrotactile Feedback to the Human Arm, Jan. 2006, Institute of Robotics and Mechatronics German Aerospace Center (DLR) Oberpfaffenhofen D-82234 Wessling (Year: 2006).*

Tong et al., Two-point orientation discrimination versus the traditional two-point test for tactile spatial acuity assessment, Sep. 13, 2013, Frontiers in Human Neuroscience, vol. 7 Article 579, pp. 1-11 (Year: 2013).*

Ogrinc et al., Sensory Integration of Apparent Motion Speed and Vibration Magnitude, Jul.-Sep. 2018, IEEE, IEEE Transactions on Haptics, vol. 11, No. 3, pp. 455-463 (Year: 2018).*

Kim et al., The Gesture Watch: A Wireless Contact-free Gesture based Wrist Interface, 2007, IEEE, 1-4244-1453-9/07/$25.00 © 2007 IEEE (Year: 2007).*

Spelmezan, D., Jacobs, M., Hilgers, A., & Borchers, J. (Apr. 2009). Tactile motion instructions for physical activities. In Proceedings of the SIGCHI conference on human factors in computing systems (pp. 2243-2252). ACM. https://hci.rwth-aachen.de/materials/publications/spelmezan2009b.pdf.

Tong, J., Mao, O., & Goldreich, D. (2013). Two-point orientation discrimination versus the traditional two-point test for tactile spatial acuity assessment. Frontiers in human neuroscience, 7, 579. https://pdfs.semanticscholar.org/5288/295ce6d58df72e4360ad5fiff2a2fce7aa71.pdf https://en.wikipedia.org/wiki/Two-point_discrimination.

Written Opinion of the International Searching Authority, dated May 4, 2016.

Extended European Search Report of the European Patent Office, dated May 24, 2018.

Anonymous: "TrekAce", You Tube, Aug. 3, 2015 (Aug. 3, 2015), pp. 1-9, XP054978367, URL:https://www.youtube.com/watch?time_continue=3&v=A0ZwuzWHol pp. 1-9.

Anonymous: "TrekAce: What is TrekAce?", Jul. 25, 2015, pp. 1-5, XP055477853, retrieved from Internet: URL: http://web.archive.org/web/20150725225507/http://www.trekace.com:80/technology/what-is-trekace/ p. 1-3.

Anonymous: "TrekAce: Fishing &Hunting", Jul. 26, 2015, pp. 1-5, XP055477855; URL:http://web.archive.org/web/20150726229112/http://www.trekace.com:80/fishing-and-hunting pp. 1-3.

Anonymous: "TrekAce: Explore" Jul. 26, 2015 pp. 1-5, XP055477856 retrieved from Internet: URL: http://web.archive.org/web/20150726777056/httpl/www.trekace.com:80/technology/explore/ p. 1-3.

Anonymous: "TrekAce: How does it work?" pp. 1-5, XP055477857 retrieved from Internet: URL: http://web.archive.org/web/20150726102311/http://www.trekace.com:80/technology/how-does-it-work/ p. 1-3.

Anonymous: "TrekAce: Frequently Asked Questions" pp. 1-5, XP055477858 retrieved from Internet: URL: http://web.archive.org/web/20150725225445/http://www.trekace.com:80/technology/frequently-asked-questions/ p. 1-3.

* cited by examiner

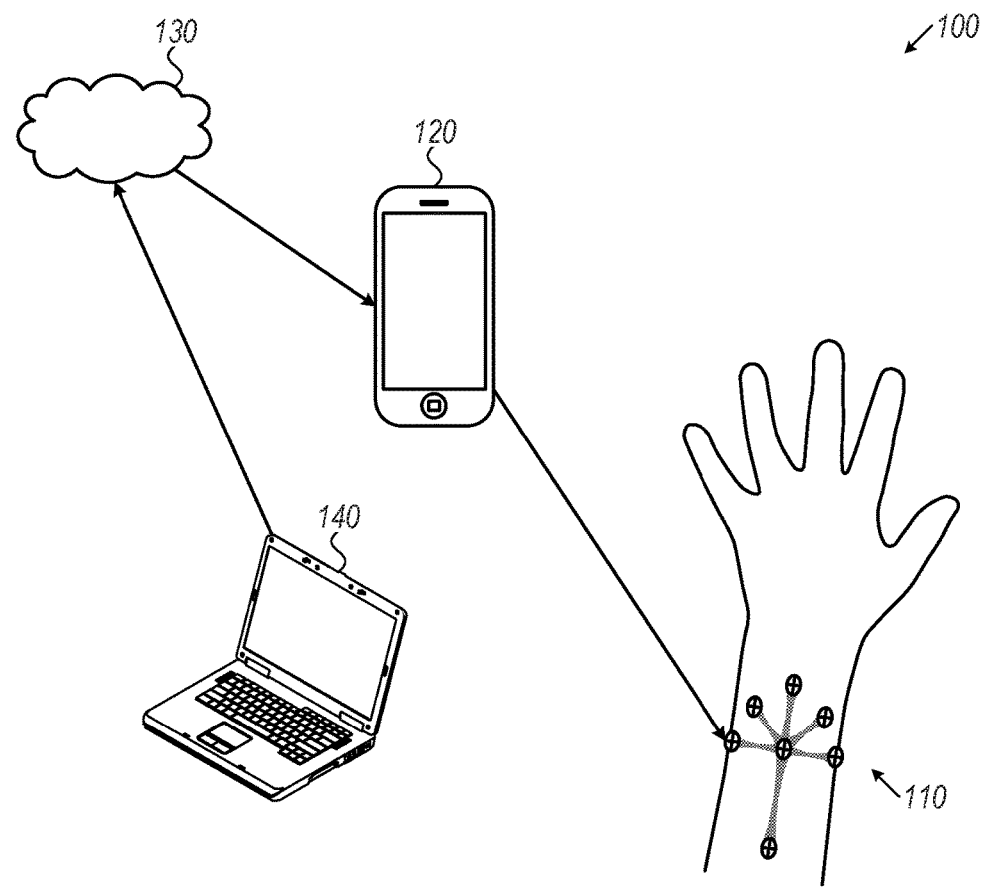
FIG. 1
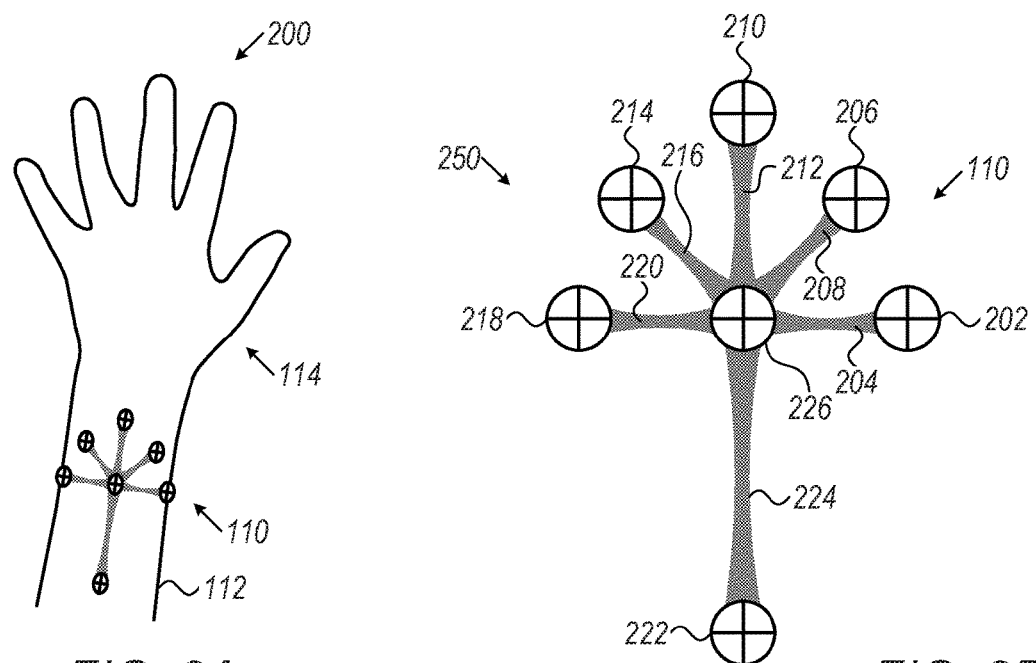
FIG. 2A
FIG. 2B

NAVIGATIONAL DEVICE AND METHODS

FIELD OF THE INVENTION

The present invention relates generally to portable navigation devices and methods, and more specifically to wearable devices for navigation.

BACKGROUND OF THE INVENTION

At present, extreme, sports and military navigation are practiced either by memorizing a route on a map, by holding and reading a physical map, or by following visual and/or sound directions of a given navigation computerized application. These available practices are not practical for certain types of extreme, sport and military navigation scenarios and conditions. Often, they are ineffective in directing the user to his target accurately, on time and safely.

Most prior art systems relay and employ subjective skills such as cognitive abilities (e.g. intelligence, perception of space, natural orienteering, etc.) and weak, easy to disrupted, senses such as vision and sound: The resulting navigation experience of prior art devices is that they are demanding and often fail due to environmental disturbances to the user.

The prior art technique of memorizing a route on a map is a practice which requires subjective orientation skills, intensive learning and training and considerable preparation time before the navigation. Moreover, while navigating on an unmarked route at natural/wild/hostile environments, it becomes a difficult task even for professionals. Mistakes and misdirection are common, obliging the hiker, athlete or soldier to stop and open an actual map (or a computerized navigation application). This costs them time, disqualification in competitions and military courses, their professional reputation, and may even create grave danger at hostile military scenarios while stopping and illuminating the map.

Holding and reading a physical map is a practice which is impractical for sport, extreme and military navigation scenarios and conditions, as it requires the hiker, athlete or soldier to continuously stop and open an actual map and thus costing them time, disqualification in competitions and military courses, their professional reputation, and may cause grave danger at hostile military scenarios while stopping and illuminating the map.

Visual directions—as in holding and reading a physical map, this practice is irrelevant for sport, extreme and military navigation scenarios and conditions as it requires the hiker, athlete or soldier to continuously stop and look at the actual map and thus costing them time, disqualification in competitions and/or military courses, their professional reputation, and may create grave danger at hostile military scenarios while stopping and using an illuminated screen.

There are also several wearable devices offering visual based indications for navigation (alongside vibration based indications). These applications hold the same described limitations and are even less practical as they employ tiny wrist-fitted screen, obliging the hiker, athlete or soldier to watch and focus on tiny visual indications while they are at a hectic environment requiring their optimal attention.

Verbal sound directions—this practice is irrelevant or less practical for sport, extreme and military navigation scenarios and conditions as it requires the hiker, athlete or soldier to focus on listening to the instructions while they are at a noise-hectic environment and need to be listening to their sound-rich environment, such as radio communication, conversations, potential threats, targets, animals in hunting, the weather, and even music, in the case of some athletes.

Vibration directions—there are several wearable devices offering vibration-based navigation. These ones namely offer a wristband comprising a plurality of haptic feedback devices arranged around a circumference of the wristband. This practice is irrelevant or less practical for sport, extreme and military navigation scenarios and conditions as the vibrating directions are of plurality of complex sensations imposed on one narrow area surrounding one hand and thus it requires the hiker, athlete or soldier to be extremely focused on (and attentive for) various complex sensations pulsing on a narrow segment of one of their hands: All that, while they are practically overwhelmed by stimulations from all senses all over their body (E.g. noises, rain, beatings, wounds, cold, heat, etc.) and by high-adrenaline sensations and emotions (fear, pain, aggressiveness, etc.). In other words, in the intense context of real life the hiker, athlete or soldier act in, they practically cannot differentiate between the concentrated vibrations and thus to translate the vibrations to actual directions; as the vibrations are limited to a too narrow area on the wrist.

WO 2014099004A1 describes an apparatus, method and other techniques for a wearable navigation device. For example, an apparatus may comprise a wristband comprising a plurality of haptic feedback devices arranged around a circumference of the wristband and logic to wirelessly receive navigation information from a computing device and to output the navigation information using one or more of the plurality of haptic feedback devices, the output comprising a mechanical representation of the navigation information. Other embodiments are described and claimed.

There is therefore an unmet need of a device capable of providing unmistakable, distinguished directional commands, without the need for verbal and/or visual instructions.

SUMMARY OF THE INVENTION

It is an object of some aspects of the present invention to provide a device and method for providing clear understandable, distinguished directional instructions, without verbal, visual, or written instructions.

In some embodiments of the present invention, improved methods and apparatus are provided for providing instructions, without auditory or visual instructions.

In other embodiments of the present invention, a method and system is described for providing tactile instructions, without auditory or visual instructions.

In additional embodiments of the present invention, a method is described for providing tactile instructions from a device placed on an arm of a user.

In yet further additional embodiments of the present invention, a method is described for providing tactile instructions from a device placed over a forearm of a user.

In further additional embodiments of the present invention, a method is described for providing tactile instructions from two devices, each placed on a forearm of a user.

The present invention provides, according to some embodiments, a wearable navigation forearm-band for intuitive navigation at sport, extreme, and military scenarios and conditions. The device guides and leads a user or a group of users, such as a hiker, a hunter, an athlete or a soldier to his destination. The device is constructed and configured to provide tactile instructions, without distractions and with optimal considerations to the extreme circumstances and conditions that the user is experiencing.

According to some embodiments of the present invention, there is provided a computerized mobile device (such as a cellphone, laptop, tablet, Smartphone or the like) carried by the user, which is adapted to process navigation information, and that is adapted to communicate by wired and/or wireless connection with at least one device. The device may be, according to some embodiments, a forearm-band sensation device.

The forearm-band sensation device is specifically invented, designed and developed to deal with the extreme circumstances and conditions users are experiencing in sport, extreme and military navigation scenarios and conditions, as well as assisting disabled users, such as the blind, aged and Alzheimer's disease patients trying to navigated while at clinical extreme circumstances and conditions.

According to some embodiments of the present invention, the device is adapted to be forearm-mounted, leaving ones hands totally free for any other task.

According to some embodiments of the present invention, the device is multi-sensory. It vibrates and flashes to ergonomically guide the user. It is simple and provides clear instructions, which assist one, without superfluous data. It is shockproof and water-resistant. It is designed and built to withstand harsh environments. The design thereof is intuitive, being simple understand and operate. It is safe and provides distraction-free navigation, eliminating a requirement to stop and look at a map and/or focus on complex signals.

According to some embodiments of the present invention, the device provides covert night-time navigation support, as the light indicators can be disabled to remain night-covert, that is, navigation without the need for any sound and/or visual indications. Thus by turning off the led emitters, the user may navigate while covert, silent and with no light exposure. The device comprises long-life life batteries for more than 20 hours operation in normal usage and the batteries may be rechargeable.

According to some embodiments of the present invention, the device's revolutionary six directional arms' operational layout is geared to achieve optimal distance between the sensations, enabling the user to easily differentiate between the physical directions' instructions, and further to provide 360 degree bearing coverage.

According to some additional embodiments of the present invention, the device comprises at least one tactile stimulus provider such as a micro-vibrator an electric vibes provider, a skin scratching element and the like, and combinations thereof, placed on the tip of each directional arm and the vibrations are ergonomically funneled to a specific point on the users forearm; resulting in a feel akin to being poked in the skin, as if someone was physically pointing and leading you.

This extraordinary layout creates a natural, intuitive user experience (UX), as the user can immediately use it without studying or training. The revolutionary design and intuitive user experience (UX) combination yields an efficient, practical navigation methodology by which, and based on the speed of the user, the device physically indicates and alerts the user before a required turn and where to head straight on.

According to some additional embodiments of the present invention, the device is suitable for use in a defense setting. It is suitable for situational awareness challenges; field performance, stealth support and seamless implementation.

According to some additional embodiments of the present invention, the device is suitable for use in military navigation (Day/Night), in which the user is subjected to harsh field conditions and to the elements. He/she may be carrying heavy equipment, may be stressed by time constrains and needs to be attentive to the surroundings and to stealth requirements.

Situational Awareness—The user needs to be in constant awareness of its definite location, location on trail, time/distance countdowns, environment information, the locations and position of his team-mates, and the like.

According to some additional embodiments of the present invention, the device is suitable for seamless implementation and offers a simple Application Program Interface (API), enabling it to easily work with many other navigational applications or devices (proprietary military navigation solutions, third party navigation Apps or other wearable devices—e.g. heart rate measurement devices).

There is thus provided according to an embodiment of the present invention, a portable navigation system for provision of navigation indications to a user, the system including;

a) at least one portable device, each device including at least four tactile stimulus components, each component disposed on an inner face of the device, each on an end portion of an extremity of a body of the device, each component adapted to impact on a specific area of skin of a user to provide at least one direction-specific instruction of movement to the user; and b) a communication apparatus adapted to provide instructions to the at least one device, wherein the at least one device is adapted to receive commands from the communication apparatus to activate the at least four tactile stimulus components, responsive to a position of the user.

Additionally, according to an embodiment of the present invention, the at least one device is wearable.

Furthermore, according to an embodiment of the present invention, the at least one device is wearable on at least one forearm of the user.

Further, according to an embodiment of the present invention, the at least one device includes two devices, each adapted to be worn on a separate forearm of the user.

Yet further, according to an embodiment of the present invention, each device of the at least one device include at least two tactile stimulus components.

Moreover, according to an embodiment of the present invention, each device of the at least one device include at least four tactile stimulus components.

Additionally, according to an embodiment of the present invention, each device of the at least one device include at least four tactile stimulus components.

Further, according to an embodiment of the present invention, the at least six tactile stimulus components are vibration elements, each adapted to vibrate on the specific area of skin on the forearm, wherein the specific areas of skin are disposed at least 2 cm away one from the other.

Yet further, according to an embodiment of the present invention, the at least six tactile stimulus components are vibration elements, each adapted to vibrate on the specific area of skin on the forearm, wherein the specific areas of skin are disposed at least 3 cm away one from the other.

Still yet further, according to an embodiment of the present invention, the specific areas of skin are disposed at least 4 cm away one from the other.

Additionally, according to an embodiment of the present invention, the communication apparatus is configured to activate different tactile stimulus components to instruct the user with different instructions.

Moreover, according to an embodiment of the present invention, the at least one portable device extremities include flexible arms.

Further, according to an embodiment of the present invention, the flexible arms each includes a visual stimulus component disposed therein.

Yet further, according to an embodiment of the present invention, the flexible arms each includes a visual stimulus component disposed thereupon.

Furthermore, according to an embodiment of the present invention, each the visual stimulus component includes at least one light emitting diode (LED) or other light devices (not LED).

Further, according to an embodiment of the present invention, at least one of the at least one light emitting diode (LED) is configured to be activated by the communication apparatus responsive to the position of the user.

Additionally, according to an embodiment of the present invention, the communication apparatus is configured to activate different visual stimulus components to instruct the user with different instructions.

Moreover, according to an embodiment of the present invention, the communication apparatus is selected from a cell phone, a smart phone, a tablet, a laptop computer, a mobile communication apparatus, a portable communication apparatus, a radio phone and an army phone.

Additionally, according to an embodiment of the present invention, the at least one portable device weighs less than 300 grams and the communication apparatus weighs less than 200 grams.

Further, according to an embodiment of the present invention, the at least one portable device weighs less than 200 grams and the communication apparatus weighs less than 100 grams.

Additionally, according to an embodiment of the present invention, the system includes a plurality of portable devices, each device adapted for use of a different user in a group, wherein one user is a leader of the group.

Furthermore, according to an embodiment of the present invention, the at least one portable device weighs less than 100 grams and the communication apparatus weighs less than 400 grams.

Additionally, according to an embodiment of the present invention, the communication apparatus is adapted for the leader control to follow movements of the users of the group.

Moreover, according to an embodiment of the present invention, the system includes a device suitable for attachment to a dog, and wherein the communication apparatus is adapted for handling by the user, the user being a handler of the dog.

There is thus provided according to another embodiment of the present invention, a language for providing instructions to a user, the language including a plurality of combinations of tactile stimuli, each stimulus provided to a different part of a forearm of the user, wherein each the tactile stimuli combination provides only one instruction to the user.

Additionally, according to an embodiment of the present invention, the instructions are movement instructions.

Moreover, according to an embodiment of the present invention, the instructions are provided by a portable navigation system including a portable device including at least four tactile stimulus components.

Furthermore, according to an embodiment of the present invention, the instructions include navigational instructions.

Further, according to an embodiment of the present invention, the instructions are directional instructions, selected from move forwards, move backwards, move right, move left, stop moving and start moving and combinations thereof.

Importantly, according to an embodiment of the present invention, the directional instructions are suitable for walking, running, trekking, swimming, cycling, driving, riding, hearing-disabled person navigation, sight-disabled person navigation, blind dog navigation, police, rescue and military dog navigation, disabled person navigation, Alzheimer disease patient navigation and combinations thereof.

Additionally, according to an embodiment of the present invention, the directional instructions are suitable for a hiker, a sight-disabled person, a dog, a hearing-disabled person, a soldier, a policeman, a guard, a sportsperson, an athlete and combinations thereof.

Furthermore, according to an embodiment of the present invention, the instructions are non-directional instructions.

Moreover, according to an embodiment of the present invention, the instructions include movement instructions.

Additionally, according to an embodiment of the present invention, the movement instructions are selected from the group consisting of a go-slow command, a go faster command, a stop command, a start moving command, a group divide command, a group merge command, a start trek command, a finish trek command and combinations thereof.

The present invention will be more fully understood from the following detailed description of the preferred embodiments thereof, taken together with the drawings.

BRIEF DESCRIPTION OF THE DRAWINGS

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is a simplified schematic illustration of a tactile instructions system for navigation, in accordance with an embodiment of the present invention;

FIG. 2A is a simplified schematic illustration of an upper view of a tactile instructions device of the system of FIG. 1, in accordance with an embodiment of the present invention;

FIG. 2B is a simplified schematic illustration of a lower view of a tactile instructions device of FIG. 2A, in accordance with an embodiment of the present invention;

FIG. 3A is a simplified schematic illustration of an upper view of another tactile instructions device of the system of FIG. 1, in accordance with an embodiment of the present invention;

FIG. 3B is a simplified schematic illustration of a lower view of the tactile instructions device of FIG. 3A, in accordance with an embodiment of the present invention;

FIG. 4A is a simplified schematic illustration of an upper view of a twin tactile instructions device of the system of FIG. 1, in accordance with an embodiment of the present invention;

FIG. 4B is a simplified schematic illustration of a lower view of the twin tactile instructions device of FIG. 4A, in accordance with an embodiment of the present invention;

FIG. 5A is a simplified schematic illustration of an upper view of another twin tactile instructions device of the system of FIG. 1, in accordance with an embodiment of the present invention;

FIG. 5B is a simplified schematic illustration of a lower view of the twin tactile instructions device of FIG. 5A, in accordance with an embodiment of the present invention;

FIG. 6 is a simplified schematic illustration of a forearm navigation indication methodology from a device of the system of FIG. 1, in accordance with an embodiment of the present invention;

FIG. 7 is a simplified schematic illustration of an upper view of a tactile instructions device of the system of FIG. 1, in accordance with an embodiment of the present invention;

Figure 8:
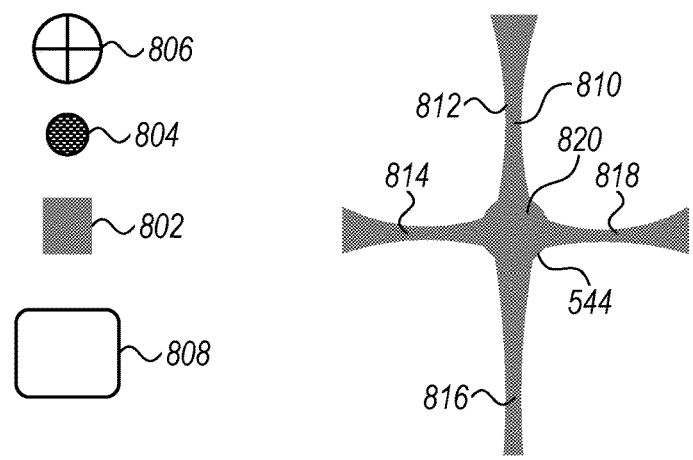
Figure 9:
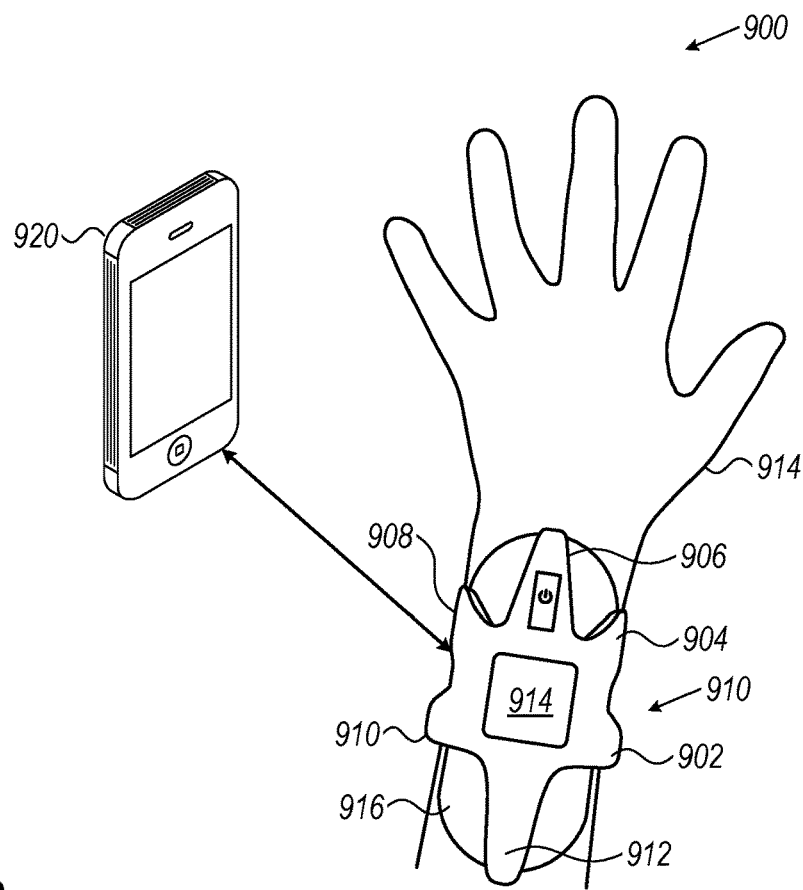
Figure 10A:
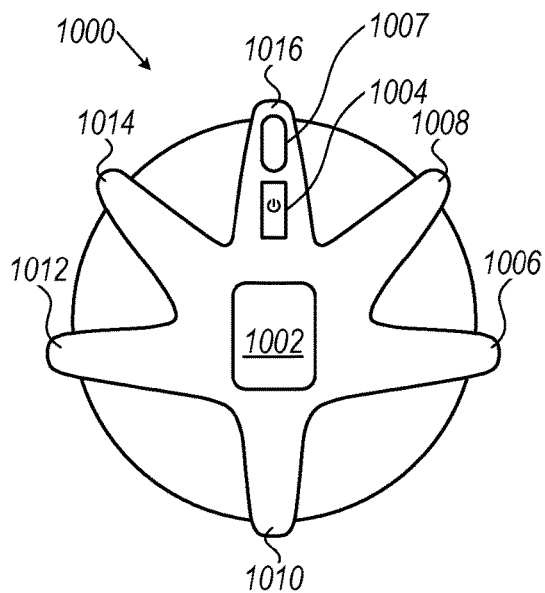
Figure 10B:
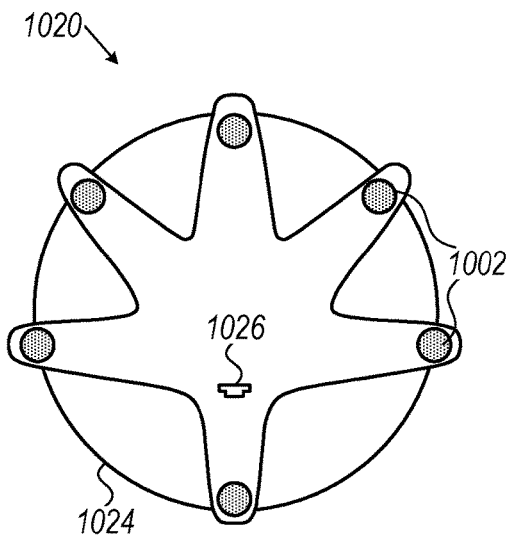
Figure 10C:
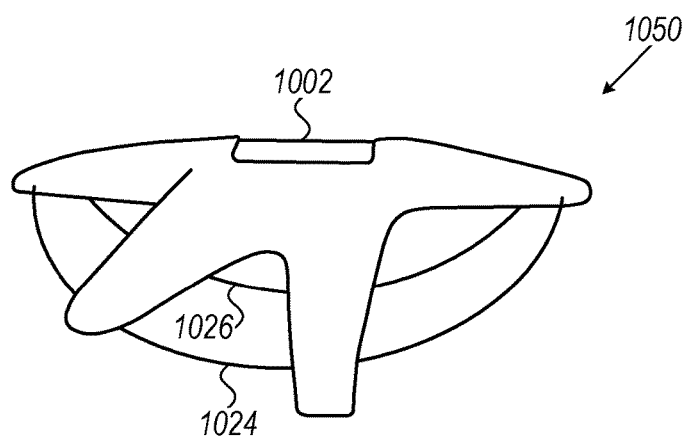
Figure 11A:
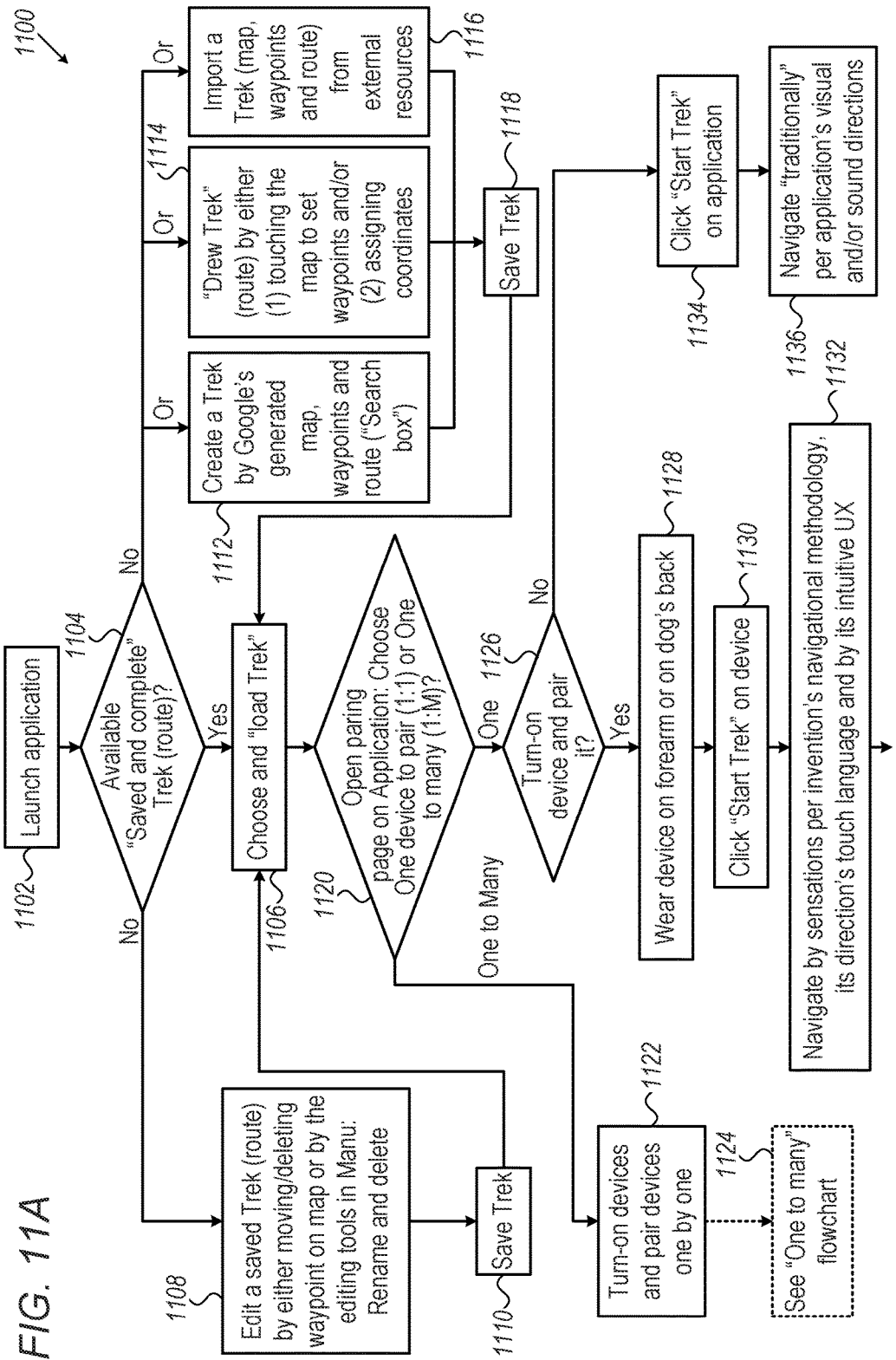
Figure 11B:
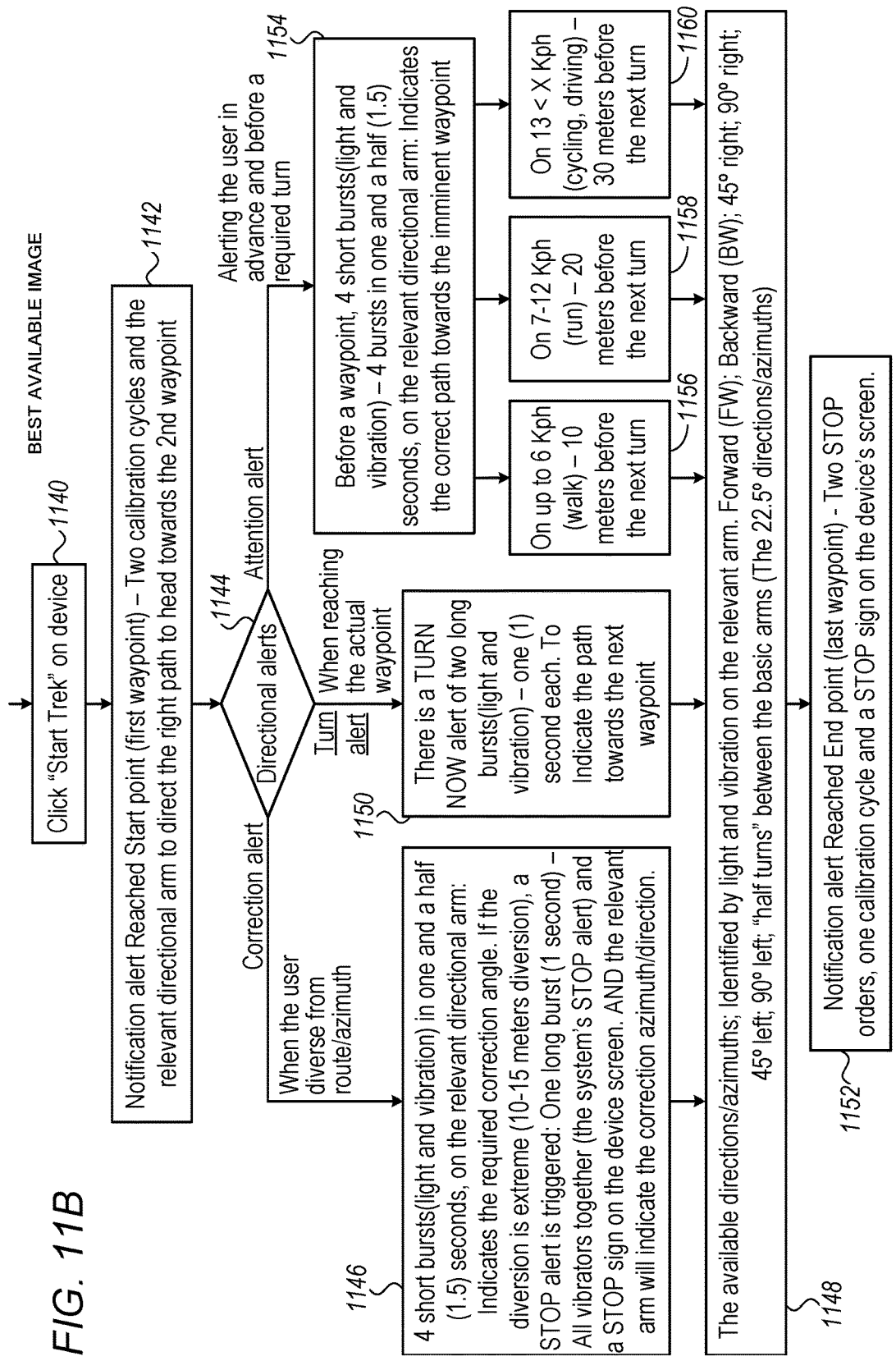
Figure 12A:
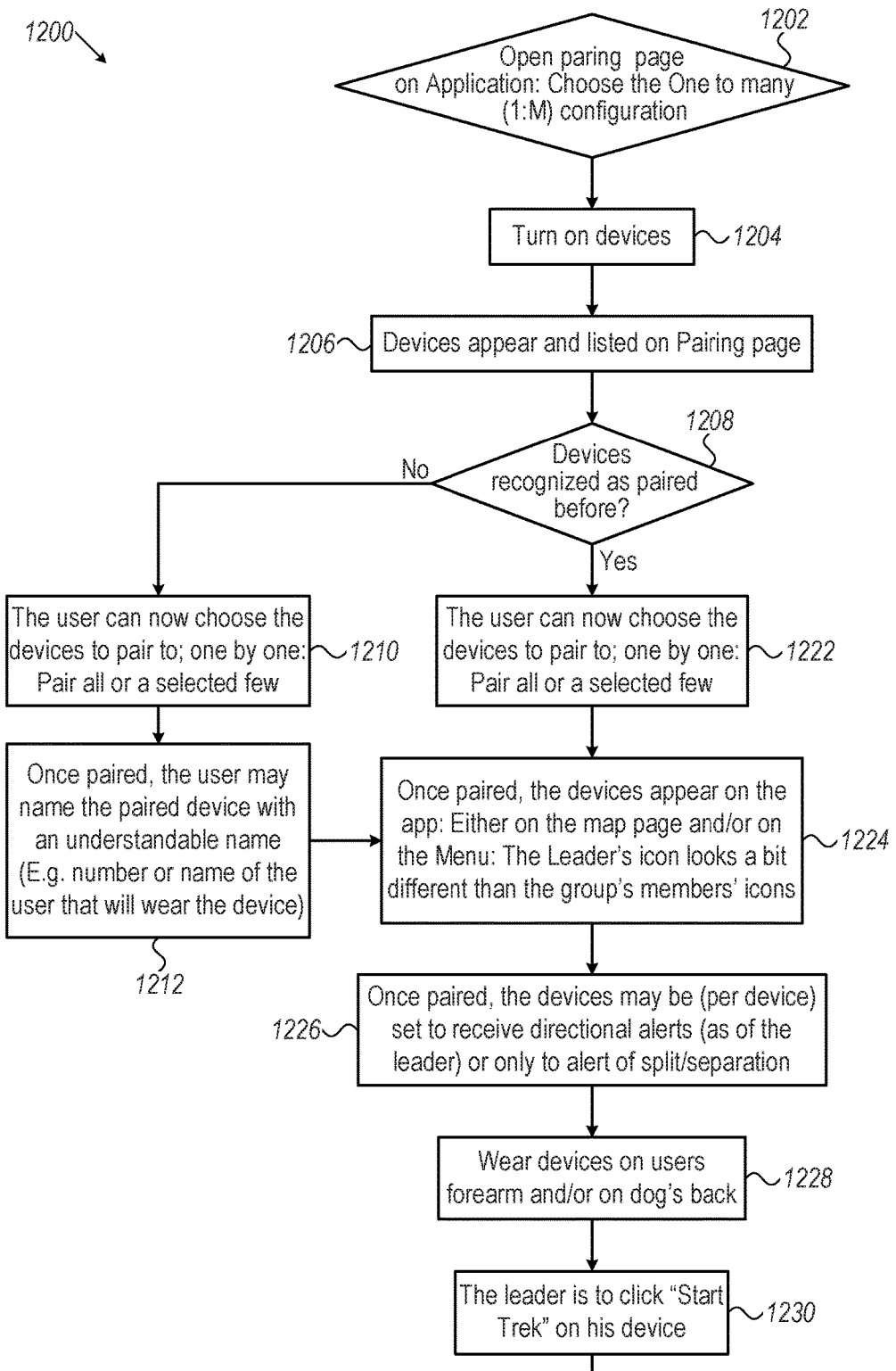
Figure 12B:
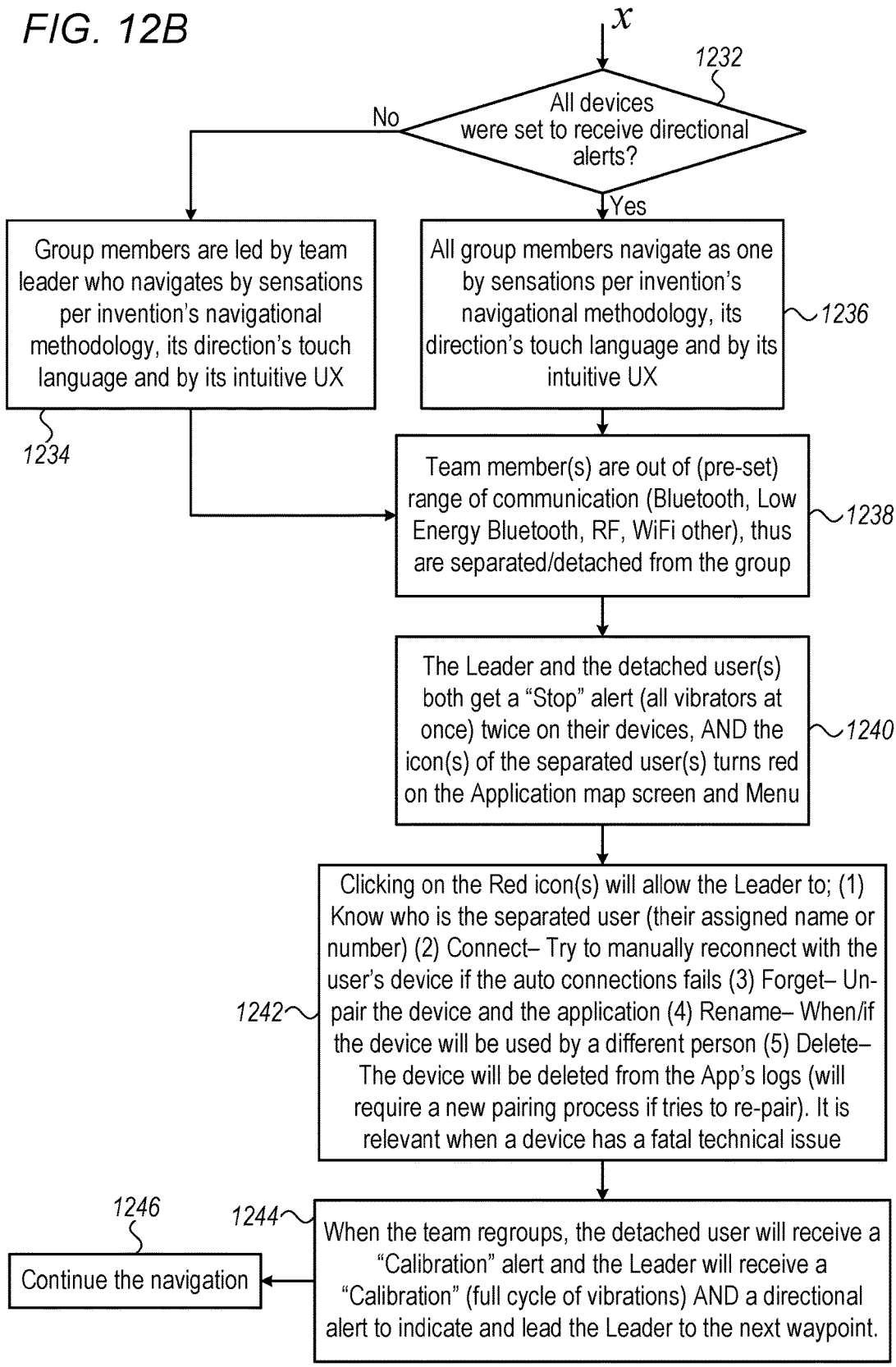
Figure 13A:
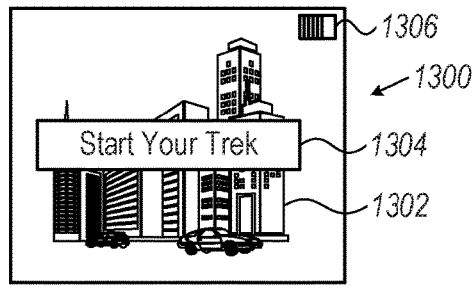
Figure 13B:
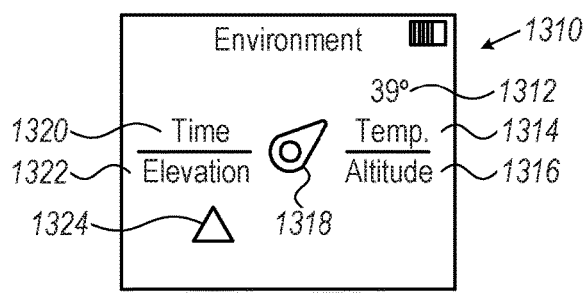
Figure 13C:
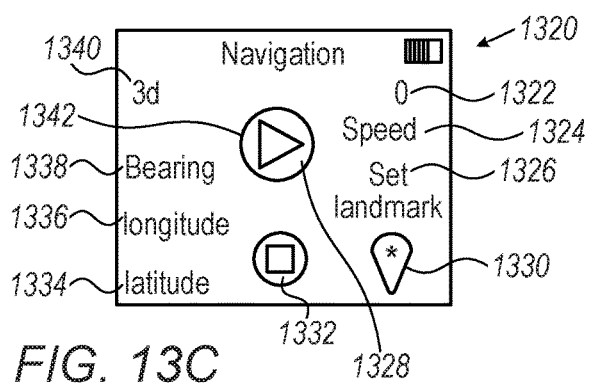
Figure 13D:
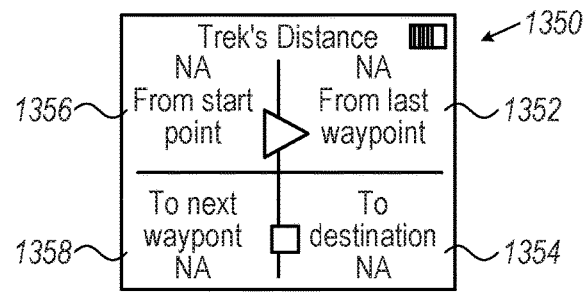
Figure 13E:
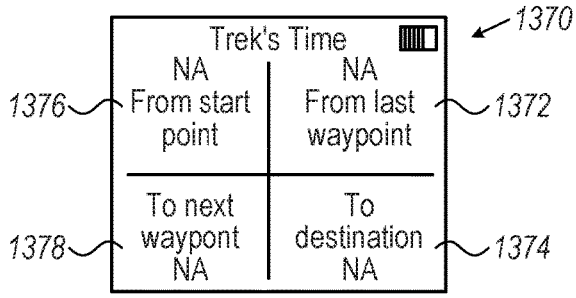
Figure 14:
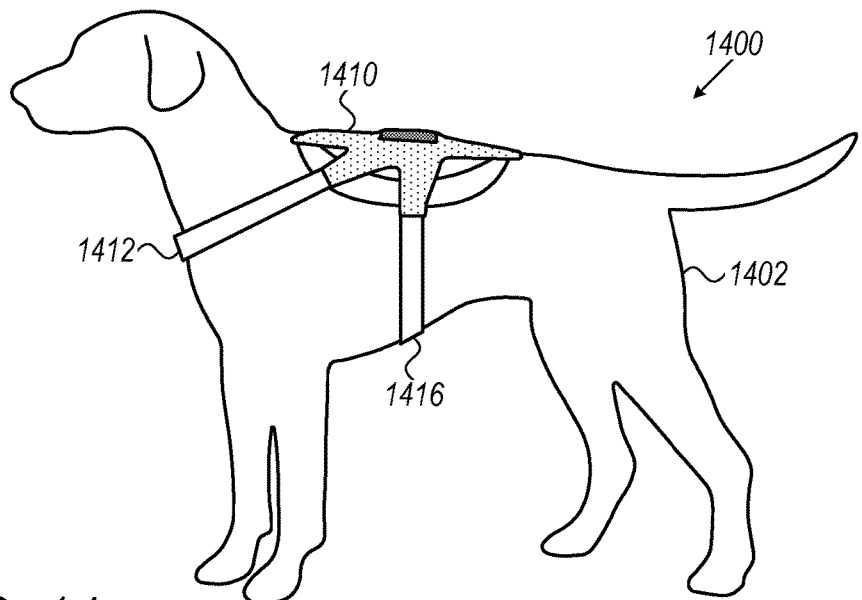
Figure 15A:
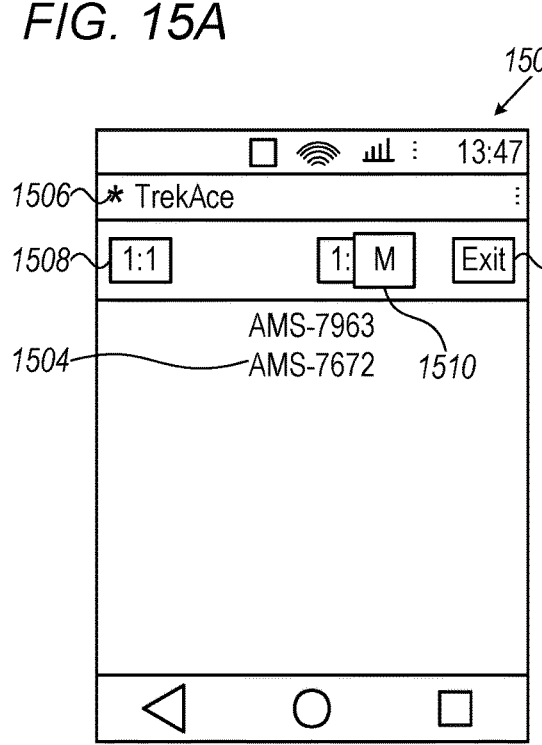
Figure 15B:
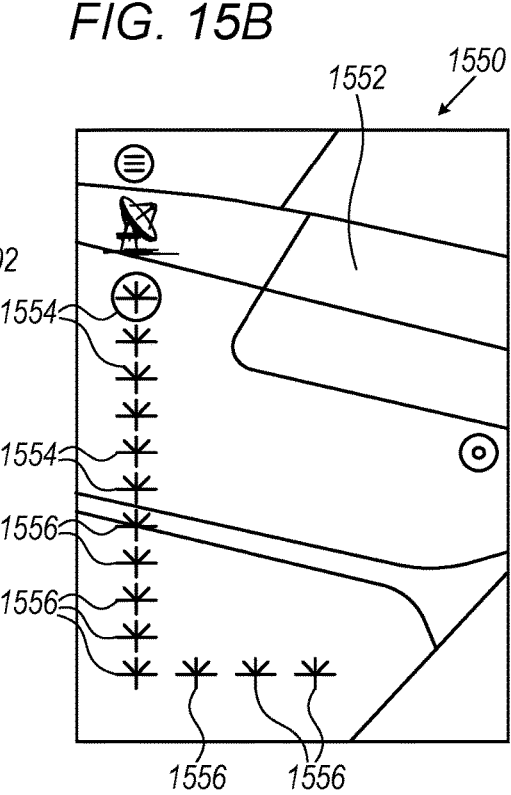

FIG. 8 shows schematic simplified illustrations of some of tactile instructions device components, in accordance with an embodiment of the present invention;

FIG. 9 is a simplified schematic illustration of another tactile instructions system for navigation, in accordance with an embodiment of the present invention;

FIG. 10A is a simplified schematic illustration of an upper view of a tactile instructions device of the system of FIG. 9, in accordance with an embodiment of the present invention;

FIG. 10B is a simplified schematic illustration of a lower view of a tactile instructions device of FIG. 10A, in accordance with an embodiment of the present invention;

FIG. 10C is a simplified schematic illustration of a side view of a tactile instructions device of FIG. 10A, in accordance with an embodiment of the present invention;

FIGS. 11A and 11B show a simplified schematic illustration of flowchart of a method for tactile navigation instruction, in accordance with an embodiment of the present invention;

FIGS. 12A and 12B show a simplified schematic illustration of flowchart of a method for group tactile navigation instruction, in accordance with an embodiment of the present invention;

FIG. 13A-13E are simplified screen shots on the tactile instructions device of the system of FIG. 1, in accordance with some embodiments of the present invention;

FIG. 14 is a simplified schematic illustration of a tactile instructions device on a dog, in accordance with an embodiment of the present invention;

FIG. 15A is a screen shot of a smartphone application screen for a group leader of the system of FIG. 1, in accordance with an embodiment of the present invention; and FIG. 15B is another screen shot of a smartphone application screen for a group leader in the system of FIG. 1, in accordance with an embodiment of the present invention.

In all the figures similar reference numerals identify similar parts.

DETAILED DESCRIPTION OF THE EMBODIMENTS

In the detailed description, numerous specific details are set forth in order to provide a thorough understanding of the invention. However, it will be understood by those skilled in the art that these are specific embodiments and that the present invention may be practiced also in different ways that embody the characterizing features of the invention as described and claimed herein.

Reference is now made to FIG. 1, which is a simplified schematic illustration of a tactile instructions system 100 for navigation, in accordance with an embodiment of the present invention.

The Present invention includes a computerized mobile device 120 (e.g. laptop 140, tablet, Smartphone 120, etc.) carried by the user, which is adapted to process navigation information, and that is adapted to communicate (by wire or wireless) with at least one device 110. The device may be constructed and configured to provide at least one tactile stimulus to an arm 110 of the user. The tactile stimuli may be selected from vibrations, electrical pulses, electrical shocks, movement of a surface against the skin of the arm and combinations thereof.

Many different types of devices are envisaged, as are exemplified herein. Typically, data is transmitted to and from the laptop/tablet/smartphone via a public network 130. Mobile device 120 is operative to transfer data directly to and from device 110.

The device is also termed herein a "forearm-band sensation device". It is specifically designed and developed to deal with the extreme circumstances and conditions the user is experiencing at sport, extreme and military navigation scenarios and conditions.

The forearm-band sensation device is specifically designed and developed to enable intuitive navigation by the user despite the extreme circumstances and conditions the user is experiencing at sport, extreme and military navigation scenarios and conditions.

The forearm-band sensation device is specifically designed and developed to enable intuitive navigation by the user while overwhelmed by stimulations from all senses all over the body, such as noises, rain, beatings, wounds, cold, heat and the like and by high-adrenaline sensations and emotions such as fear, pain and aggressiveness.

The invented forearm-band sensation device is specifically designed and developed to separate, distinguish and differentiate between the sensations (vibration and/or flicker or other tactile stimuli as detailed hereinabove) and thus enabling the user to easily comprehend the directions and thus to intuitively navigate at sport, extreme and military scenarios and conditions.

Reference is now made to FIG. 2A, which is a simplified schematic illustration of an upper view 200 of a tactile instructions device 110 of system 100 of FIG. 1, in accordance with an embodiment of the present invention. The device is adapted for placing on a forearm of a user. When the user is human, the devices dimensions are typically 10-40 cm in length, 5-20 cm in width, and has a thickness of 0.1-80 mm. The device may be made, in part out of a flexible polymer, such as rubber, silicone, plastic, a textile, a fabric and combinations thereof. When the device is for an animal, the dimensions are adjusted to match a body or leg of the animal. For example, for a dog-see FIG. 14 hereinbelow.

Turning to FIG. 2B, there can be seen a simplified schematic illustration of a lower view 250 of a tactile instructions device 110 of FIG. 2A, in accordance with an embodiment of the present invention. Device 110 comprises a plurality of micro-vibrators 202, 206, 210, 214, 218, 222 and 226. Additionally or alternatively these may be providers of other tactile stimuli, as exemplified herein. Most or all of the micro-vibrators are disposed on the tip of "arms" 204, 208, 212, 216, 220 and 224. These may optionally extend radially from a central micro-vibrator 226. The arms are made, in part out of a flexible polymer, such as rubber, silicone, plastic, a textile, a fabric and combinations thereof.

Figure 3A:
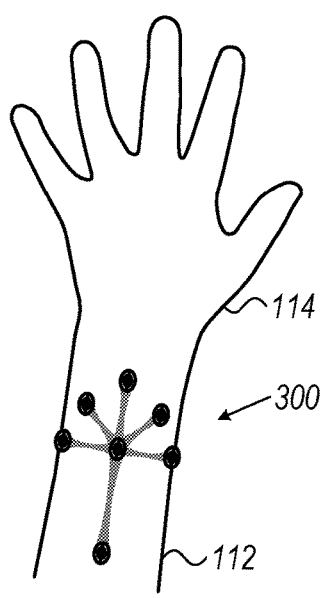

FIG. 3A is a simplified schematic illustration of an upper view of another tactile instructions device 300 of system 100 of FIG. 1, in accordance with an embodiment of the present invention.

Figure 3B:
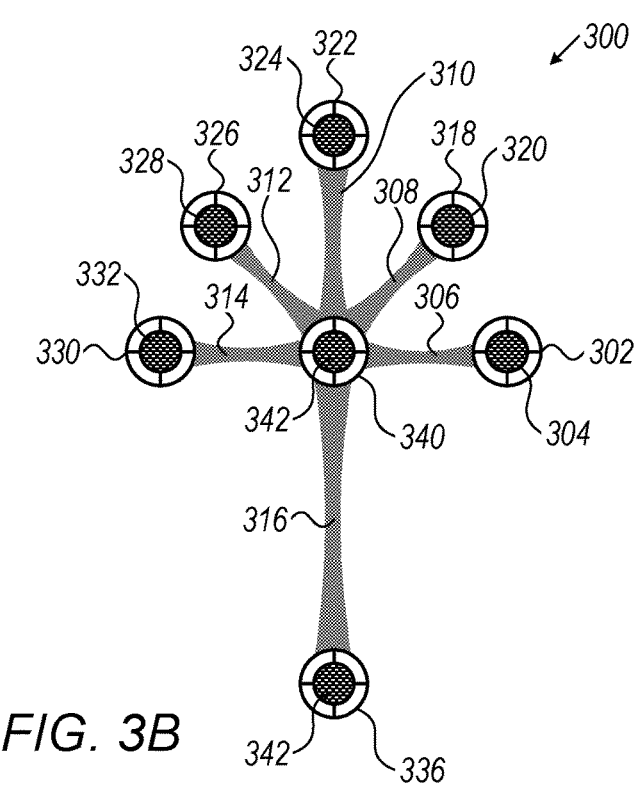

FIG. 3B shows an illustration of a lower view of tactile instructions device 300 of FIG. 3A, in accordance with an embodiment of the present invention. Device 300 comprises a plurality of micro-vibrators 304, 320, 324, 328, 330, and 334. Most or all of the micro-vibrators are disposed on "arms" 308, 310, 312, 312, 314 and 316 extending radially from a central micro-vibrator 342.

Additionally, each micro-vibrator has one of more light emitting diodes (LEDS) 302, 318, 322, 326, 332, 336 and 334 associated therewith (the LED emitters may be placed anywhere on the arms not only on the tip, as illustrated here).

The micro-vibrators are typically facing downwards to touch the skin of arm 112. The LEDs may be facing upwards and of different color lights. The arms are made, in part out of a flexible polymer, such as rubber, silicone, plastic, a textile, a fabric and combinations thereof. Thus, device 300 is constructed and configured to provide instructions by at least one of a tactile and visual sense, and combinations thereof. For example, the device may be configured to provide only tactile stimuli during daylight and tactile and visual stimuli at night or within buildings. Furthermore, the light may be tuned off to support night-covert operation.

Figure 4B:
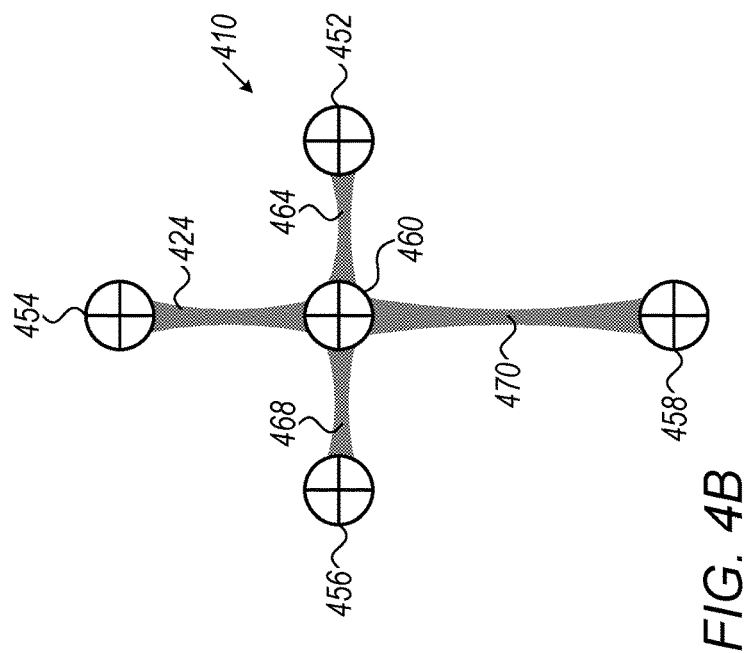
Figure 4A:
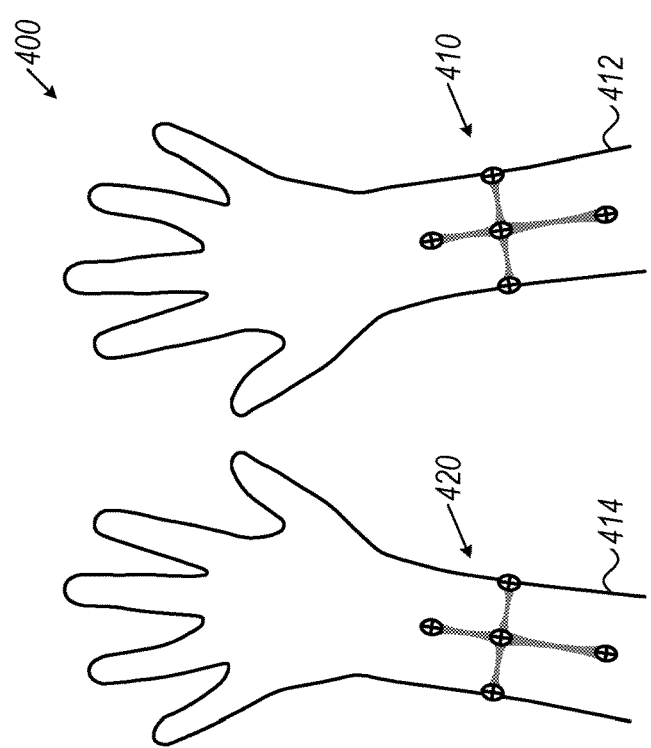

Reference is now made to FIG. 4A, which is a simplified schematic illustration of an upper view of a twin tactile instructions device 400 of the system of FIG. 1, in accordance with an embodiment of the present invention. The twin device comprises a first device 410 and a second device 420. This twin device is constructed and configured to provide instructions by at least one of a tactile and visual sense, and combinations thereof. For example, the device may be configured to provide only tactile stimuli during daylight and tactile and visual stimuli at night or within buildings. Furthermore, the light may be tuned off to support night-covert operation. The tactile stimuli may be selected from vibrations, electrical pulses, electrical shocks, movement of a surface against the skin of the arm and combinations thereof. The exemplification in the drawings of "vibrators" should not be deemed limiting. The two-arm configuration presents a different embodiment of a directions methodology to that of the one-arm methodology.

FIG. 4B shows a lower view 450 of twin tactile instructions device 400 of FIG. 4A, in accordance with an embodiment of the present invention. Device 400 comprises a plurality of micro-vibrators 452, 454, 456, 458, and 460. Most or all of the micro-vibrators are disposed on "arms" 464, 466, 468 and 470 extending radially from a central micro-vibrator 460. The arms are made, in part out of a flexible polymer, such as rubber, silicone, plastic, a textile, a fabric and combinations thereof.

Figures 5A, 5B:
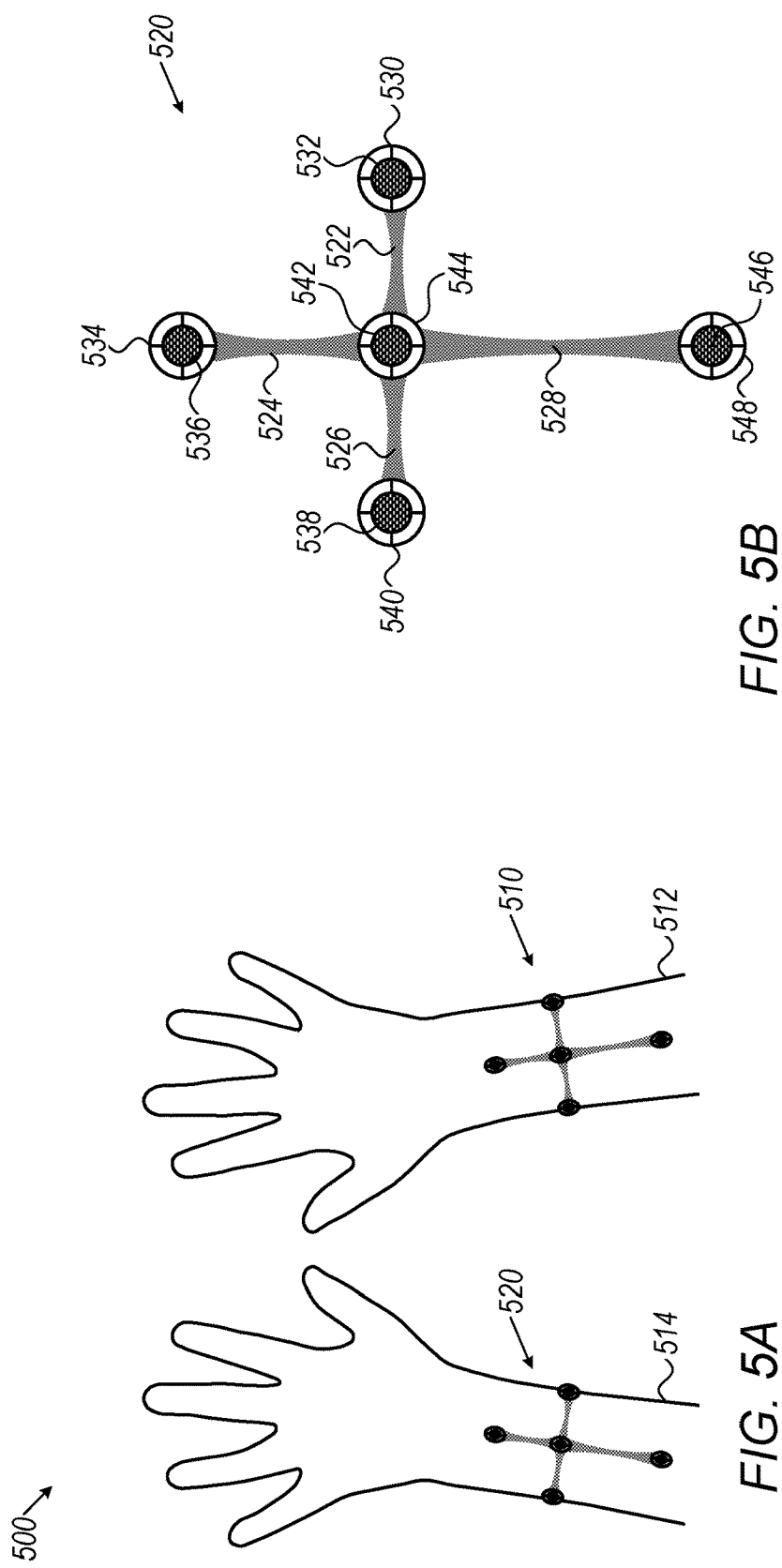

Reference is now made to FIG. 5A, which is a simplified schematic illustration of an upper view of another twin tactile instructions device 500 of system 100 of FIG. 1, in accordance with an embodiment of the present invention. FIG. 5B shows a lower view 520 of twin tactile instructions device 500 of FIG. 5A, in accordance with an embodiment of the present invention.

Devices 510, 520 each comprise a plurality of micro-vibrators 532, 534, 538, 542 and 546. Most or all of the micro-vibrators are disposed on "arms" 522, 524, 526 and 528 extending radially from central micro-vibrator 542.

Additionally, each micro-vibrator has one of more light emitting (LEDS) 530, 536, 540, 544 and 548 associated therewith. The micro-vibrators are typically facing downwards to touch the skin of arm 112. The LEDs may be facing upwards and of different color lights. Arms 522, 524, 526 and 528 are made, in part out of a flexible polymer, such as rubber, silicone, plastic, a textile, a fabric and combinations thereof. Thus, twin device 500 is constructed and configured to provide instructions by at least one of a tactile and visual sense, and combinations thereof. For example, the device may be configured to provide only tactile stimuli during daylight and tactile and visual stimuli at night or within buildings.

The twin device (Device 400) may provide a set of instructions to the user. These may be, according to some embodiments, navigational and movement instructions. For example, a. Straight Forward—The two front micro-vibrators (or other tactile stimuli) and/or LED emitters are vibrating/flashing on both hands/forearms.
b. 90° Right Turn—The right-side micro-vibrator/LED emitter on the right hand ONLY is vibrating/flashing.
c. 90° Left Turn—The left-side micro-vibrator/LED emitter on the left hand ONLY is vibrating/flashing.
d. 45° Right Turn—Only the front micro-vibrator/LED emitter on the right hand ONLY is vibrating/flashing.
e. 45° Left turn Only the front-vibrator/LED emitter on the left hand ONLY is vibrating/flashing.
f. Straight Backward—The two rear micro-vibrators/LED emitters are vibrating/flashing on both hands/forearms.
g. Stop—ALL micro-vibrators/LED emitters on both hands are vibrating/flashing.

Figure 6:
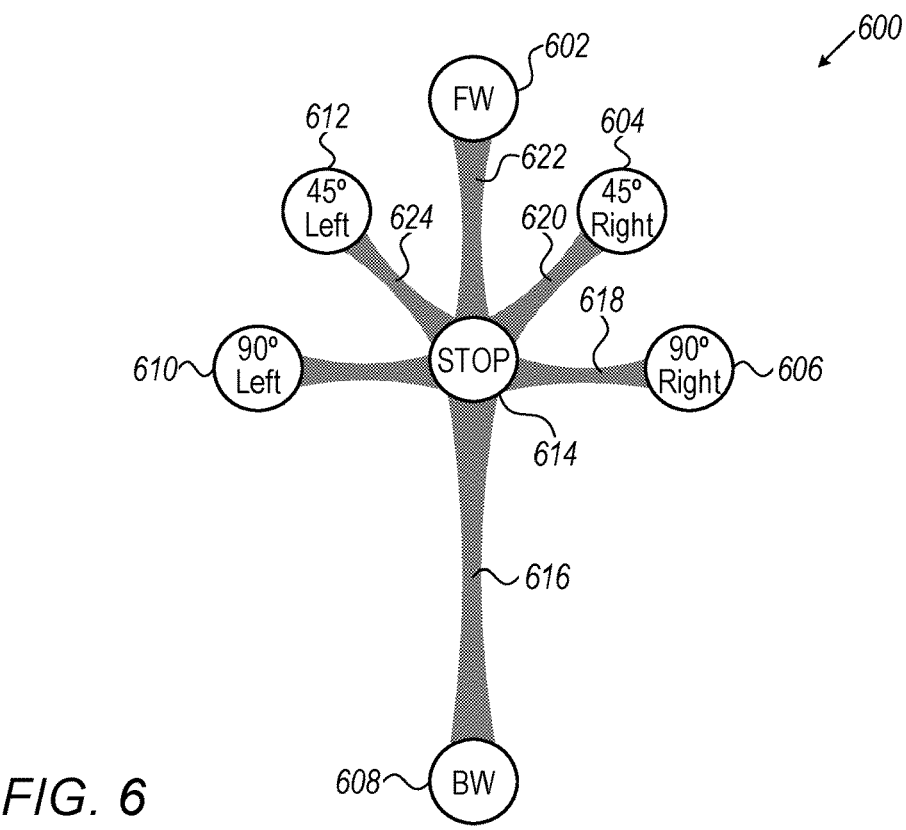

Reference is now made to FIG. 6, which is a simplified schematic illustration of a forearm navigation indication methodology from a device 110 of system 100 of FIG. 1, in accordance with an embodiment of the present invention.

In a one-hand configuration by device 110 (FIG. 1), the "forearm-band" device has six or optionally seven stimulator elements 602, 604, 606, 608, 610, 612 and 614. These include stimulator element 602 to make a straight forward step or steps, stimulator element 604 to make a 45 degree right step or steps, stimulator element 606 to make a 90 degrees right step or steps, stimulator element 608 to take a backwards step or steps, stimulator element 610 to make a 90 degrees left step or steps, stimulator element 612 to make a 45 degree left step or steps. It should be understood that the stimuli may be combinations of stimuli. Thus, device 110 is constructed and configured to provide instructions by at least one of a tactile and visual sense, and combinations thereof. For example, the device may be configured to provide only tactile stimuli during daylight and tactile and visual stimuli at night or within buildings.

The devices of the present invention are often constructed with the following design features.

1. Each stimulator element is disposed at a point, which is as remote as possible from the center point and from each other in order to have the vibrations separated, distinguished and differentiated.
2. Each point is at the end of an arm on an "Octopus" layout.
3. The layout uses the size of a forearm to separate the sensation points as much as possible.
4. When enabled, the LED emitters may flicker in a plurality (such as nine) different colors per each of the plurality (such as nine) possible directions.

Figure 7:
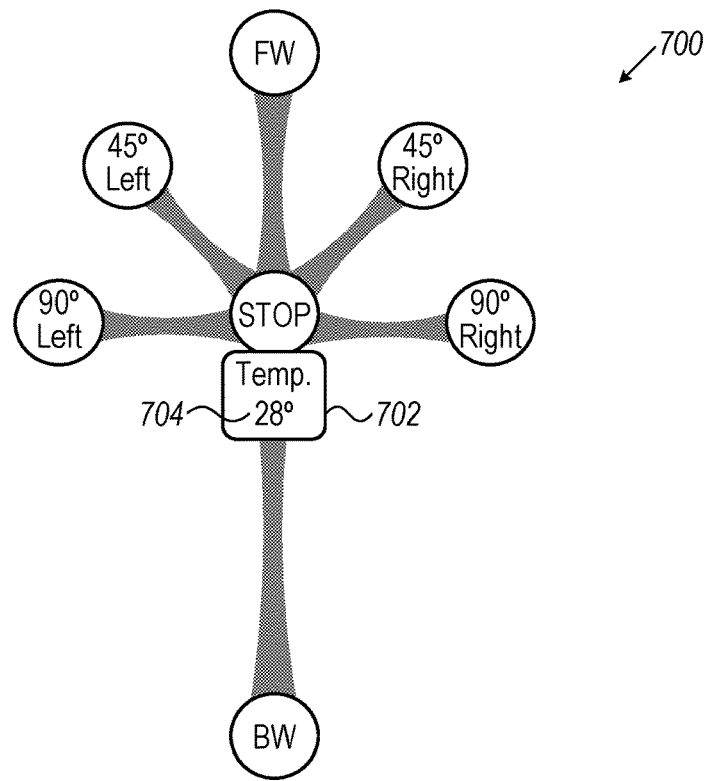

Reference is now made to FIG. 7, is a simplified schematic illustration of an upper view of another tactile instructions device 700 of system 100 of FIG. 1, in accordance with an embodiment of the present invention. Device 700 comprises a centrally disposed screen 702, for providing one or more readouts 704. The screen is typically small touch screen and is operative to display relevant information, such as a local time, an electronic compass, actual longitude/latitude information, an ambient temperature and the like. The device is constructed such that the screen may be disabled/enabled per the navigation context and circumstances, such as in a military context versus when hiking.

FIG. 8 shows simplified schematic illustrations of some of tactile instructions device components 802, 804, 806, 808, 810, 812, 814, 816, 818 and 820, in accordance with an embodiment of the present invention. Some non-limiting examples of components of the devices of the present invention include an RF/WiFi/Bluetooth component 802, an LED emitter component 804, a micro-vibrating component (or other) 806, a screen component 808, and material/polymeric support/structural components 810, 812, 814, 816, 818 and 820.

Reference is now made to FIG. 9 is a simplified schematic illustration of another tactile instructions system 900 for navigation, in accordance with an embodiment of the present invention.

Device 910 comprises a plurality of arms 902, 904, 906, 908, 910 and 912 disposed around a centrally placed screen 914. Most or all of the micro-vibrators (not seen) are on the lower side tip of these arms. Device 910 is in communication with smartphone 920 (or any other suitable communication device). This may be one or more of non-wired and wired communication between the phone and the device. An application (not shown)—in smartphone 920 is operative to provide the location of the user wearing/carrying device 910 and overlay his/her location onto a pre-defined route on a map. The user is then able to receive directional commands, routes and maps from the server or locally saved on the Smartphone to at least one of the smartphone and device 910.

Reference is now made to FIG. 10A, which is a simplified schematic illustration of an upper view of a tactile instructions device 1000 of system 900 of FIG. 9, in accordance with an embodiment of the present invention. The device may comprise an on/off button 1004. According to some embodiments, button 1004 is a two functions button, such that a quick depression thereof will turn the device on/off, a longer push will activate at least one flashlight 1007. The device further comprises a screen for displaying information such as, but not limited to:

a) Environmental information—local time, ambient temperature, altitude, route/terrain information, and elevation,
b) Navigational information, compass directions, azimuth, longitude/latitude, current speed, landmark settings,
c) Trek's Distance, from start point, from last waypoint, to next waypoint, to destination, and
d) Trek's time from start point, from last waypoint, to next waypoint, to destination.

FIG. 10B shows a lower view 1020 of tactile instructions device 1000 of FIG. 10A, in accordance with an embodiment of the present invention. The device may comprise a peripheral strengthening band 1024 and tactile elements (not shown) disposed on some/all of the arms. The tactile elements may be vibrators and/or other suitable stimulating elements. The device further comprises a Micro USB socket 1026, used for charging and for receiving and sending data (while on wired configuration with the Smartphone et. al devices).

FIG. 10C is a simplified schematic illustration of a side view 1050 of tactile instructions device 1000 of FIG. 10A, in accordance with an embodiment of the present invention. The device may have dimensions of 14 cm in width, adjustable 10-50 cm in length, using a strap, like a watch strap, buttons, studs, Velcro or any other suitable fastening means (not shown). The thickness of the device may be 1.3 cm.

Reference is now made to FIGS. 11A and 11B, which show a simplified schematic illustration of flowchart of a method 1100 for tactile navigation instruction, in accordance with an embodiment of the present invention.

The user/team leader launches a navigation application in the smart phone 120, in a launching application step 1102.

He/she checks to see if there is an available "saved and complete" trek (route) in checking step 1104.

If yes, he proceeds to step 1106, if no, he has the options to proceed to edit a saved Trek route in an editing trek step 1108. He edits a saved trek (route) by either moving/deleting waypoint on map or by the editing tools in application's menu. He may optionally rename and/or delete the trek.

In a saving trek step 1110, he saves the edited trek on the smartphone's application.

Another optional step is to create a trek using a Google-generated map, waypoints and route ("search box") in a trek creating step 1112.

Another optional step is to create a new trek by "drawing trek step 1114" (route) by either (1) touching the map to set waypoints and/or (2) assigning coordinates Another optional step is an import a trek step 1116 by importing one or more of a map, waypoints and one or more route from external resources via the internet on smartphone or via a removable SD card 120.

After steps 1112, 1114 or 1116, the user saves the trek in another saving trek step 1118.

Thus, he can now choose and "load trek" in a choosing and loading trek step 1106.

The user may be alone, with a dog, or with a team/group. He therefore has to choose the appropriate configuration for setting up the trek.

He opens a paring page in the application to define the number and type of trek participants in a "choosing one or many step" 1120 (choose one device to pair (1:1) or one to many (1:M)?). Accordingly, he must choose how many devices need to be paired. If there is a group of trek participants, he asks the group members to switch on their portable/wearable devices 110, 700, 910 in an activating devices step 1122. Thereafter, he proceeds with the method of FIGS. 12A and 12B, described hereinbelow.

If the user is to use a wearable device for the trek, or for example a dog 1402 is to wear a device 1400, then the user activates the device in step 1126 and pairs it with his device via the application in smartphone 120 (FIG. 1). If there is no wearable device to pair, then he proceeds to a starting trek step 1134. He then navigates "traditionally" per the application's visual and/or sound directions in a traditional navigating step 1136.

If there is a paired device, then he puts a device 1400 on his forearm (or on the dog's back (FIG. 14)) in a putting on step 1128.

He then clicks "start trek" on device 1400 or portable devices 110, 700, 910.

He navigates by sensations per invention's navigational methodology, its direction's touch language and by its intuitive UX in a navigating step 1132.

In an activating step 1140, he then click "start trek" on the cellphone or wearable device. The wearable device begins to provide tactile instructions to the. user, man or dog, that moves, in accordance to the wearable device's directional instructions towards the Start point (First waypoint). Once reaching the first waypoint, the user receives a notification alert in an alerting step 1142; "you have reached the start point (first waypoint)" by means of two calibration cycles and activation of the appropriate directional arm (vibrator and/or LEDs) to direct the user to right path to head towards a second waypoint.

The user (and optionally a dog) move towards the second waypoint. He then receives directional alerts in a second alerting step 1144. For example, before a new waypoint, the portable device emits four short bursts (light and vibration) in another attention alerting step 1154—4 bursts in one and a half (1.5) seconds, on an appropriate directional arm of the device-indicating the correct path and direction towards the next imminent waypoint.

When the user diverts from his route/azimuth, he receives a correction alert in a correcting step 1146. For example, the portable device emits four short bursts (light and vibration) for one and a half (1.5) seconds, on the relevant directional arm of the device, indicating the required correction angle.

If, for example the diversion is extreme (10-15 meters diversion), a STOP alert is triggered: One long burst (1 second)—All vibrators together (the system's STOP alert) and a STOP sign on the device screen, followed by a correction alert on the relevant arm of the wearable device indicates the correction azimuth/direction to be followed immediately by the user.

When the user actually reaches the correct waypoint, he/she receives a "turn now" instruction in instructing step 1150. For example, the wearable device provides a "TURN NOW" alert of two long bursts (light and vibration)—one (1) second each. to indicate the path/angle of movement towards the next waypoint in the trek.

Moreover, further alerts are provided in alerting step 1156, when moving at up to 6 Kph (walking)—10 meters before the next notification alert, alerting step 1158, At 7-12 Kph (run)—20 meters before the next turn, and at 13<X Kph (cycling, driving)—30 meters before the next turn, alerting step 1160.

When reaching a final destination a notification alert step 1152 indicates that the user has reached an end point (last waypoint). For example, two STOP orders, one calibration cycle and a STOP sign on the device's screen.

Throughout the trek, the available directions/azimuths are identified by light and vibration on the relevant arm of the wearable device, by the user in alerting steps 1148. These include Forward (FW); Backward (BW); 45° right; 90° right; 45° left; 90° left; "half turns" between the basic arms (The 22.5° directions/azimuths).

Reference is now made to FIGS. 12A and 12B, which show a simplified schematic illustration of flowchart of a method 1200 for group tactile navigation instruction by a team leader, in accordance with an embodiment of the present invention.

In an opening pairing page step 1202, the leader/user opens a paring page on application on smartphone 120 and he/she chooses the "One to many (1:M) configuration".

Thereafter, all members in the group switch on their portable/wearable devices 110, 700, or 910 in an activating step 1204.

These devices will be listed on a pairing page of the application on Smartphone 120, in a listing step 1206.

In a checking step 1208, the devices listed in step 1206 and recognized, are checked to see if they have been used as paired before.

If yes, the user can now choose the devices to pair to; a) one by one, b) pair all or c) pair a selected few, in a choosing pairing technique step 1222.

Once paired, the user may name the paired device with an understandable name (e.g. number or name of the user who is to wear the device) in a naming step 1212.

Once paired, the named devices appear on the app in an uploading device name step 1224, either on a map page (FIG. 15B) and/or on the Menu (FIG. 15A): The leader's icon 1554 looks a bit different than the other group members' icons 1552. Once paired, the devices may be (per device) set to receive directional alerts (as of the leader) or only to alert of separation/split (step 1226).

The leader may wear the device on his forearm, the users may put on their devices and/or a device may be put on dog's back in a wearing step 1228.

The group is now ready to go and the leader click a "Start Trek" button on his device in a starting trek step 1230.

In a testing device step 1232, it is checked to see if all devices are set to receive directional alerts. If yes, all group members navigates together as one by sensations per invention's navigational methodology, its direction's touch language and by its intuitive UX, in a directing step 1236.

If no, group members are led by team leader who navigates by sensations per invention's navigational methodology, its direction's touch language and by its intuitive UX, in a leading step 1234.

Thereafter, it often occurs that team member(s) are out of (pre-set) range of communication (Bluetooth, Low Energy Bluetooth, RF, WiFi other), thus are separated/detached from the group, in a "lose part of the group step" 1238.

In a stopping step, 1240, the leader and the detached user(s) both get a "Stop" alert (all vibrators at once) twice on their portable devices, AND the icon(s) of the separated user(s) turns red on the Application map screen and Menu on smartphone 120 (FIG. 1).

The leader tries to regroup by trying to minimize the distance from the detached user(s) and/or in an attempting to regroup step 1242 by clicking on the red icon(s) of the separated user(s) on the application. This allows the leader to; (1) Know who is the separated user (their assigned name or number) (2) Connect—Try to manually reconnect with the user's device if the auto connections fails (3) Forget—Un-pair the device and the application (4) Rename—When/if the device will be used by a different person (5) Delete—The device will be deleted from the App's logs (will require a new pairing process if tries to re-pair). It is relevant too, when a device has a fatal technical issue.

In a regrouping step 1244, when the team regroups, the detached user will receive a "Calibration" alert and the Leader will receive a "Calibration" (full cycle of vibrations) AND a directional alert to indicate and lead the Leader to the next waypoint.

Thereafter, in a continuing the trek step 1246, the group continues the navigation.

Reference is now made to FIG. 13A-13E, which are simplified screen shots 1300, 1310, 1320, 1350, and 1370 on touch-screen 202 of the tactile instructions device 700 of the system of FIG. 1, in accordance with some embodiments of the present invention.

Screenshot 1300—Start your trek-opening screen. After pairing the application on the mobile communication device 120 (FIG. 1) and the tactile instructions device 700, clicking "Start your trek" will begin the navigation via device 700. Typically it will show a text 1304, a picture or image 1302 and an on/off button 1306. The embedded application then leads to a second screen 1310 "the environment".

Environment-second screen 1310: Presents a compass (center arrow) 1318, a time of day ("Time") 1320, an ambient temperature ("Temp.") 1312 or other temperature 1314, an elevation (shows the degree of elevation 1322—up or down shown by an arrow—of current location versus a next waypoint, an altitude 1316 above sea level.

This leads to a third screen 1320—a navigation screen, which presents a bearing in degrees 1338, a speed of the user 1322, a current longitude 1336, a current latitude 1334, Play/Pause 1332 and stop of the navigation, enabling the user to set a new waypoint (on the go) by clicking the set landmark button 1330. The new Waypoint will be added to the Trek and the system will lead the user from the newly created Waypoint to the next one.

This leads to a fourth screen 1350 Trek's Distance, which presents a current distance from a start point 1356, a current distance from a last way point 1352, a current distance to the next waypoint 1358 and a remaining distance to a destination (final waypoint) 1354.

This leads to a fifth screen 1370 (Trek's Time) and presents a running time from a start point 1376, a running time from a last waypoint 1372, a remaining time, per average speed of the user to a next waypoint 1378 and a remaining time to a final destination 1374.

Reference is now made to FIG. 14, which is a simplified schematic illustration of a tactile instructions device 1400 on a dog 1402, in accordance with an embodiment of the present invention. The device comprises a number of straps 1412, 1416, attached to arms 1410 of the device. for attaching it to the dog's body.

Dog handling and direction—

Visually-impaired user support—The current practice of a guide dog supporting a visually impaired person is primarily of helping the person to avoid obstacles. With a device of the present invention placed on the dog's back, and with basic training, the dog may now lead the visually impaired person to its destination and thus to become a complete solution of both leading and guiding.

Police, rescue and military support dog—the current practice of a sending a dog to a remote task is by either walking next to it or by placing a camera and speaker from which the handler is commanding the dog: Walking next to it—places the human handler in harm's way and thus undermine the reason for the usage of police/military dogs. The prior art practice of placing a camera and speaker on a dog is as with human navigators. The practice employs sound directions, on which the dog should rely. These employ the weak, easily disrupted, senses, such as vision and sound. These result in a navigation experience that is demanding and subjected to environmental disturbances. With a device of the present invention device placed on the dog's back, and with basic training, the dog may now be directed to the destination without a human escort or by the easy to be disrupted sound directions.

Memory-disabled user support (e.g. Alzheimer's disease)—weary or memory-disabled people may be supported by the device of the present invention. There is no need to remember the way home. Simply wear it on the forearm and be led home.

In summary, the devices of the present invention are constructed and configured to provide a user with:

a) distraction-free navigation—no need to stop and open a map; no need to be focused on complex signals on a limited body area (e.g. wrist);
b) night-time navigation—by eliminating the need to stop and open an illuminated map;
c) sensation-based directions only—the device of the present invention uses the sensation of touch to guide and direct. It is a much more deep and basic sense and less subjected sense than the senses of vision and sound. And thus, when under external stimulations, pressure, harsh field conditions, the elements, etc., a user of the device of the present invention can comprehend the instructions (in contrast to the users of traditional navigation tools, which tend to fail;
d) the devices provide intuitive navigation—by a simplified wearable directions' system, method and methodology;
e) Limited sensation types—Only vibrations and/or flickers (no sound or graphics)
f) Sufficient physical distance between the sensation generators (E.g. micro-vibrators and LED emitters) for distinguishing the directions.
g) Less time needed to memorize the route—The practical nature of the invention reduces the need to memorize the map or even to look at the map before the navigation
h) Like no other, the devices of the present invention are Forearm-mounted—leaving ones hands totally free for the task. Multi-sensory—it ergonomically vibrates and flashes to guide you; Simple—it has everything you need and nothing you don't; Shockproof & water-resistant—it's designed and built to withstand harsh environments; Intuitive design—easy to understand and operate; Safe, distraction-free navigation—no need to stop and look at a map or focus on complex signals; Covert night-time navigation—disable the flicker indications to remain night-covert; Long battery life—20 hours' in normal usage and rechargeable.
i) The device of the present invention holds innovations in the domains of Operational Design, User Experience (UX) practicality and Navigation Methodology:
j) Its revolutionary 6 directional arms' operational layout is geared to achieve optimal distance between the sensations, enabling the user to easily differentiate between the physical directions' instructions. And, to provide 360° bearing coverage. There are micro-vibrators placed on the tip of each directional arm and the vibrations are ergonomically funneled to a specific point on the users forearm; resulting in a feel akin to being poked in the skin, as someone is physically pointing and leading you.
k) This extraordinary layout creates a natural, intuitive User experience (UX) as the user can immediately use it without studying or training. During extensive testing, the users' comprehension was found to be immediate.
l) The revolutionary design and intuitive UX combination yields an efficient, practical navigation Methodology by which, and based on the speed of the user, the device of the present invention will physically indicate and alert the user before a required turn on where to head on.

The present invention provides systems 100, 900 and methods 1100, 1200 for intuitive navigation at sport, extreme and military scenarios and conditions.

The present invention relates generally to wearable navigation devices 110, 300 and methods, and more specifically to methods and systems for wearable navigation forearm-band for intuitive navigation at sport, extreme and military navigation scenarios and conditions.

The present invention is a wearable navigation forearm-band that guides & leads the user (or a group of users) such as a hiker, hunter, athlete or soldier to his/hers destination without distractions and with optimal considerations to the extreme circumstances and conditions the user is experiencing.

Directions Methodology—A New Language
Notification Alerts;
Reached Start point (first waypoint)—Two calibration cycles and the relevant directional arm to direct the right path to head towards the 2nd waypoint.
Reached End point (last waypoint)—Two STOP orders, one calibration cycle and a STOP sign on the device's screen.

Based on the speed of the user, the device alerts the user in advance and before a required turn. Here's how:
Attention Alert;
Before a waypoint, 4 short bursts (light and vibration)—4 bursts in one and a half (1.5) seconds, on the relevant directional arm: Indicates the correct path towards the imminent waypoint.
In up to 6 Kph (walk)—10 meters before the next turn; 7-12 Kph (run)—20 meters before the next turn; and 13<X Kph (cycling)—30 meters before the next turn.
Turn Alert;
When reaching the actual waypoint, there is a TURN NOW alert of two long bursts (light and vibration)— one (1) second each. To indicate the path towards the next waypoint.
Correction Alerts;
When the user diverts from route/azimuth—
4 short bursts (light and vibration) for one and a half (1.5) seconds, on the relevant directional arm-indicating the required correction angle.

If the diversion is extreme (10-15 meters diversion), a STOP alert is triggered: One long burst (1 second)—All vibrators together (the system's STOP alert) and a STOP sign on the device screen. Additionally, the relevant arm will indicate the correction azimuth/direction.

The five basic directions/azimuths; identified by light and vibration on the relevant arm. As exemplified in FIGS. 6 and 7. If the user needs to turn right 45 degrees, vibrator 604 vibrates. If the user needs to move 90 degrees to the right, vibrator 606 vibrates. If the model device is 300 (FIG. 3B) having lights and vibrators, then the appropriate lights and/or vibrators are activated to provide a command.

If the user wears device 910 (FIG. 9), then, for example to move 22.5 degrees to the right, arms 906 and 904 will vibrate alternatively. All devices of the present invention are constructed and configured to provide the following commands to the user by tactile and/or light instructions: —forward (FW), backward (BW), 45 degrees right, 90 degrees right, 45 degrees left and 90 degrees left.

Commands to move at an angle between the above angles are provided by vibration/lighting of two adjacent arms, such as a 22.50° move command:
Attention alert; before a turn, two (2) short bursts (light and vibration)—four (4) bursts in total in 1.75 seconds, on the two relevant directional arms. For example, in a case where a 22.50 turn to the right is required, the FW arm and the 45° to the right arm will alternatively blink and vibrate.
Turn alert; TURN NOW—2 long bursts (light and vibration)—4 bursts in total in 3 seconds (0.75 each), on the two relevant directional arms. For example, in a case where a 22.5° turn to the right is required, the FW arm and the 45 degree to the right arm will alternatively blink and vibrate 2 times each.

BEST MODES OF IMPLEMENTATION

The present invention provides systems and methods for intuitive navigation and thus is best implemented in the following examples of navigation modes:
Sport/Extreme Navigation (Day/Night)
a. Sport navigation—The user is subjected to time constrains, harsh field conditions and the elements.
b. Hiking—The user is subjected to harsh field conditions and the elements and carries heavy equipment.
c. Hunting—The user is subjected to harsh field conditions and the elements, carries heavy equipment and needs to be attentive to the surroundings.
d. Wind surfing—The user is subjected to waters conditions, the elements (and sometimes time constrains), holding and steering the board and needs to be attentive to the surroundings
e. Kayaking—The user is subjected to waters conditions, the elements (and sometimes time constrains), holding and steering the board and needs to be attentive to the surroundings.
f. On/Off-road Running—The user is subjected to time constrains, complex and/or harsh road/track conditions and the elements.
g. On/Off-road Cycling—The user is subjected to road/track conditions, the elements and time constrains, holding and steering the bicycle and needs to be attentive to the surroundings.
h. Mountain climbing—The user is subjected to harsh field conditions and the elements, carries heavy equipment and needs to be attentive to the surroundings.
i. Military Navigation (Day/Night)—
j. The user is subjected to harsh field conditions and the elements, carries heavy equipment, time constrains, needs to be attentive to the surroundings and to stealth requirements
k. Assisting Visually-Disabled/Blind Users
l. A visually disable or blind person may find the systems and devices of the present invention very useful in assisting him/her in getting around. The user is subjected to varied terrains and needs to be attentive to the surroundings.
m. Casual Urban Navigation
n. The user is in an unknown area, maze-like streets, time constrains, usually is an inexperienced navigator.
o. The user is subjected to the elements, carries equipment, time constrains, needs to be attentive to the surroundings.
p. Dog Handling and Direction
q. Visually-impaired user support—the current practice of a guide dog supporting a visually impaired person is primarily of helping the person to avoid obstacles. With a device of the present invention placed on the dog's back, and with basic training, the dog may now lead the visually impaired person to its destination and thus to become a complete solution of both leading and guiding.
r. Police, rescue and military support—the current practice of a sending a dog to a remote task is by either walking next to it or by placing a camera and speaker from which the handler is commanding the dog: Walking next to it—places the human handler in harm's way and thus undermine the reason for the usage of police/military dogs. The prior art practice of placing a camera and speaker on a dog is as with human navigators. The practice employs sound directions, on which the dog should rely. These employ weak, easily disrupted, senses, such as vision and sound. These result in a navigation experience that is demanding and subjected to environmental disturbances.

s. With a device of the present invention device placed on the dog's back, and with basic training, the dog may now be directed to the destination without a human escort or by the easy to be disrupted sound directions.

t. Memory-Disabled User Support (e.g. Alzheimer's Disease)

u. Weary or memory-disabled people may be supported by the device of the present invention. There is no need to remember the way home. Simply wear it on the forearm and be led home.

The systems of the present invention overcome the prior art requirements for visual and auditory directions as well as the requirement to hold and read a physical map in practice. Moreover, using the systems of the present invention, there is no longer a need for sound directions. Thus the user, does not need to focus and listen to the instructions while at a noise-hectic environment (from radio communication, conversations, potential threats, targets, animals in hunting, the weather, and even music, in the case of some athletes).

The systems of the present invention overcome the prior art requirements for using the prior art navigation gadgets. There are few gadgets emerging offering vibration-based navigation. The more relevant ones are urban-fashion styled bracelets, offering a wristband comprising a plurality of feedback devices arranged around a circumference of the wristband and is positioned on a narrow area of the hand—the wrist. However, in the intense context of real life the hiker, athlete or soldier act in, they practically cannot differentiate between the concentrated vibrations and thus to translate the vibrations to actual directions; as the vibrations are limited to a too narrow area on the wrist.

In sharp contrast with the prior art devices, the devices and systems of the present invention guide and lead the user thereof, such as a hiker, hunter, athlete or soldier, sight-disabled person, to his/her destination without distractions, as well as with optimized considerations to the extreme circumstances and conditions the user is experiencing.

The forearm wearable navigation devices of the present invention, separate, distinguish, differentiate and simplify the navigation indications/instructions to the user and thus creating an intuitive navigation experience.

The devices of the present invention provide sensation-based directions. As illustrated herein, there are micro-vibrators placed on the tip of each directional arm. The vibrations are ergonomically funneled to a specific point on the users forearm, resulting in a feel of a firm pointed touch on the skin, as if someone were poking the user's skin. The device also provides one or more visual indications, which can be disabled, by embedded LED emitters in each directional arm.

Materials of construction of the device—there are several cover ("shell") types. textile, silicone, rubber or a combination thereof. These provide the device with flexibility, durability, water resistance, light-weight and a slick look.

Team usages of the systems of the present invention (see FIGS. 12). When a "split" occurs in a team of users, the leader and the detached/lost user will both get a "Stop" alert (all vibrators at once) twice (a unique alert to this scenario). When the team regroups, the detached user will receive a "Calibration" alert. The leader receives a "Calibration" (full cycle of vibrations) alert and a directional alert simultaneously, to indicate and lead the leader to the next waypoint.

Integration to external devices: —the unique vibrations' language, created by the systems of the present invention, enables creation of additional alerts to indicate of additional scenarios and necessities. For example, alerting on a too fast heart's pulse-rate will alert the user by a slow pace vibration, instructing him/her to slow down.

Cellphone Applications of the Present Invention

A propriety smartphone application which is adaptable to Android, iPhone/MS Mobile or other Operational Systems is installed on the communication computerized device. Accordingly, the portable/wearable device is configured to seamlessly support and communicated with all of these platforms.

1. The app is based on a suitable map SDK or an open-source application such as Google Maps.
2. The app supports Terrain Map, off-road routs, satellite images, etc.
3. The app supports free-hand routing: the Navigator may draw his own route and navigate according to his route, including pre defined waypoints
4. Navigation routes can be shared with social networks
5. The route may be saved on the device and then be operated without internet connectivity
6. The map and route may be imported from the web or from saved files on a removable secure digital (SD) card.
7. The app supports creating on-the-go landmarks (Touch-and-Go on a button on the device)
   a. Places a pin on the map
   b. Can be shared with social networks
   c. As a landmark is set, there is an indication by an all-around-vibration and by a light on the center LED.
      The app is connected to the physical device—the forearm navigation band—by P2P wifi or Bluetooth
      ii. The app provides data to the device that is presented on its screen, such as, but not limited to a current time, compass, azimuth, temperature (C or F), altitude (measurements—US or Eu, set in apps' settings), longitude/latitude, speed, terrain/route steepness (elevation profile), distances, from start point, from last waypoint, to next waypoint and to last waypoint/destination, time from start point, from last waypoint, to next waypoint and to last waypoint/destination
   The app is constructed to receive data from the device, such as, but not limited to, receive location trigger data to create a landmark. When a landmark is set, a waypoint is created on the route and there will and indication, a green LED blinks.
8. Based on the speed of the walk/run the app will alert the user a bit before a required turn in order for him not to miss the turn—with several short vibration flicks and light flicks on the relevant directional device's arm
9. The app store historic navigation data such as time, duration, average duration per section if the trek.
10. The app supports all relevant features relevant for navigation provided by the SDK.

The references cited herein teach many principles that are applicable to the present invention. Therefore the full contents of these publications are incorporated by reference herein where appropriate for teachings of additional or alternative details, features and/or technical background.

It is to be understood that the invention is not limited in its application to the details set forth in the description contained herein or illustrated in the drawings. The invention is capable of other embodiments and of being practiced and carried out in various ways. Those skilled in the art will readily appreciate that various modifications and changes can be applied to the embodiments of the invention as hereinbefore described without departing from its scope, defined in and by the appended claims.

The invention claimed is:

1. A portable system for provision of a set of distinguishable tactile instructions to a user, the system comprising:
   a. at least one portable, hands-free, forearm-band sensation device for attachment to at least one forearm of said user, each device comprising at least four tactile stimulus components, each component disposed on an inner face of said device, each on an end portion of a flexible arm of a body of said device, each component adapted to impact on a specific area of skin of a user to provide a plurality of tactile stimuli, and wherein said at least four tactile stimulus components are adapted to provide a plurality of combinations of tactile stimuli from said end portions to said specific areas of skin, wherein each said tactile stimuli combination provides only one instruction of said set to the user, wherein said device is configured to provide unmistakable, distinguished commands, without the need for verbal and/or visual instructions; and
   b. a communication apparatus configured to be carried by the user, adapted to wirelessly communicate instructions to said at least one forearm-band sensation device and to wirelessly receive communications from said at least one forearm-band sensation device, wherein said at least one forearm-band sensation device is adapted to receive commands from said communication apparatus to activate said at least four tactile stimulus components; and
      wherein said at least one forearm-band sensation device weighs less than 200 g and said communication apparatus weighs less than 400 g, and wherein said tactile instructions are selected from movement instructions and navigational instructions.

2. A portable system according to claim 1, wherein said set of distinguishable tactile instructions are directional instructions selected from, selected from move forwards, move backwards, move right, move left, stop moving and start moving and combinations thereof.

3. A portable system according to claim 2, wherein said system is configured to guide the user via a route to a destination and said at least one device is wearable on at least one forearm of said user.

4. A portable system according to claim 3, each device comprising a touch screen adapted to display information.

5. A portable system according to claim 4, wherein said at least one device comprises two devices, each adapted to be worn on a separate forearm of said user.

6. A portable system according to claim 5, wherein each device of said at least one device comprise at least six tactile stimulus components.

7. A portable system according to claim 6, wherein said at least six tactile stimulus components are vibration elements, each adapted to vibrate on said specific area of skin on said forearm, wherein said specific areas of skin are disposed at least 2 cm away one from the other.

8. A portable system according to claim 7, wherein said communication apparatus is configured to activate different tactile stimulus components to instruct said user with different instructions.

9. A portable system according to claim 1, wherein said at least one portable device comprise six flexible arms and wherein said at least one forearm-band sensation device is shockproof and water resistant.

10. A portable system according to claim 9, wherein said six flexible arms each comprises a visual stimulus component disposed therein.

11. A portable system according to claim 10, wherein each said visual stimulus component comprises at least one light emitting diode (LED) or other light devices (not LED) and wherein at least one of said at least one light emitting diode (LED) is configured to be activated by said communication apparatus responsive to said position of said user.

12. A portable system according to claim 1, wherein said communication apparatus is adapted to communicate with said at least one portable device via at least one of a wired connection and a wireless connection; and wherein said communication apparatus is selected from a cell phone, a smart phone, a tablet, a laptop computer, a mobile communication apparatus, a portable communication apparatus, a radio phone and an army phone.

13. A portable system according to claim 12, wherein said communication apparatus further comprises an application configured to provide navigational instructions and correctional instructions if a deviation from said route is detected.

14. A portable system according to claim 1, comprising a plurality of portable devices, each device is adapted for use of a different user in a group, wherein one user is a leader of said group.

15. A portable system according to claim 14, wherein said communication apparatus is adapted for leader control of said users of said group.

16. A portable system according to claim 1, wherein said set comprises a go-slow command, a go faster command, a stop command, and a start moving command.

17. A portable system according to claim 1, wherein said set further comprises a group divide command, a group merge command, a start trek command, a finish trek command and combinations thereof.

18. A portable system according to claim 1, wherein said set of distinguishable tactile instructions comprises movement instructions.

19. A portable system according to claim 18, wherein said movement instructions are selected from the group consisting of a go-slow command, a go faster command, a stop command, a start moving command, a group divide command, a group merge command, a start trek command, a finish trek command and combinations thereof.

20. A portable system according to claim 4, wherein said information is selected from said instructions, information related to said instructions, environmental information, navigational information, trek information and combinations thereof.

21. A system according to claim 13, wherein said communication apparatus is configured to detect at least one of an altitude and an azimuth of the user.

22. A system according to claim 21, wherein navigational instructions are three-dimensional navigational instructions.

23. A system according to claim 21, wherein correctional instructions are three-dimensional correctional instructions.

24. A system according to claim 1, wherein said unmistaken distinguished commands are selected from the group consisting of navigational commands, instructional commands, informative commands and combinations thereof.

* * * * *